US011832925B2

(12) United States Patent
Lee et al.

(10) Patent No.: US 11,832,925 B2
(45) Date of Patent: Dec. 5, 2023

(54) ELECTRONIC DEVICE FOR MEASURING BIOMETRIC INFORMATION AND METHOD FOR OPERATING THE SAME

(71) Applicant: Samsung Electronics Co., Ltd., Gyeonggi-do (KR)

(72) Inventors: Hansung Lee, Gyeonggi-do (KR); Chansoo Park, Gyeonggi-do (KR); Hyunsu Hong, Gyeonggi-do (KR); Sander Land, Gyeonggi-do (KR); Jongho Park, Gyeonggi-do (KR); Hyejung Seo, Gyeonggi-do (KR); Yongjin Lee, Gyeonggi-do (KR)

(73) Assignee: Samsung Electronics Co., Ltd

( * ) Notice: Subject to any disclaimer, the term of this patent is extended or adjusted under 35 U.S.C. 154(b) by 194 days.

(21) Appl. No.: 16/797,574

(22) Filed: Feb. 21, 2020

(65) Prior Publication Data

US 2020/0268263 A1    Aug. 27, 2020

(30) Foreign Application Priority Data

Feb. 25, 2019  (KR) .................. 10-2019-0021703

(51) Int. Cl.
   *A61B 5/0295*      (2006.01)
   *A61B 5/024*       (2006.01)
   (Continued)

(52) U.S. Cl.
   CPC ........ *A61B 5/0295* (2013.01); *A61B 5/02433* (2013.01); *A61B 5/14551* (2013.01);
   (Continued)

(58) Field of Classification Search
   CPC .............. A61B 5/0295; A61B 5/02433; A61B 5/14551; A61B 5/4818; A61B 5/681;
   (Continued)

(56) References Cited

U.S. PATENT DOCUMENTS

2005/0033129 A1   2/2005  Edgar, Jr. et al.
2005/0058456 A1   3/2005  Yoo
   (Continued)

FOREIGN PATENT DOCUMENTS

JP   2007-083021   4/2007
JP   2011-067497   4/2011
   (Continued)

OTHER PUBLICATIONS

International Search Report dated Jun. 4, 2020 issued in counterpart application No. PCT/KR2020/002669, 9 pages.
   (Continued)

*Primary Examiner* — Eric F Winakur
*Assistant Examiner* — Abid A Mustansir
(74) *Attorney, Agent, or Firm* — The Farrell Law Firm, P.C.

(57) ABSTRACT

An electronic device includes a housing, a touchscreen display viewable through a first part of the housing, a photoplethysmogram (PPG) sensor exposed through a second part of the housing, a processor disposed in the housing and operatively connected to the touchscreen display and the PPG sensor, and a memory disposed in the housing and operatively connected to the processor, wherein the memory stores instructions that, when executed, are configured to cause the processor to receive first data from the PPG sensor, generate second data by band-pass filtering the first data, generate oxygen saturation data based on at least some of the second data, select a first portion related to a first period of time from the second data, and display, on the touchscreen display, a graphical user interface including information related to the oxygen saturation data except for data corresponding to the first portion from the graphical user interface.

11 Claims, 23 Drawing Sheets

(51) Int. Cl.
  *A61B 5/1455* (2006.01)
  *A61B 5/00* (2006.01)
(52) U.S. Cl.
  CPC ............ *A61B 5/4818* (2013.01); *A61B 5/681* (2013.01); *A61B 5/6843* (2013.01); *A61B 5/7221* (2013.01)
(58) Field of Classification Search
  CPC . A61B 5/6843; A61B 5/7221; A61B 5/02116; A61B 5/02416; A61B 5/7225; A61B 5/7435
  See application file for complete search history.

(56) References Cited

U.S. PATENT DOCUMENTS

| | | | |
|---|---|---|---|
| 2007/0049811 A1 | 3/2007 | Kobayashi et al. | |
| 2010/0185068 A1 | 7/2010 | Park et al. | |
| 2011/0112442 A1* | 5/2011 | Meger | A61B 5/4818 600/595 |
| 2013/0172703 A1 | 7/2013 | Dixon et al. | |
| 2014/0058229 A1* | 2/2014 | Su | A61B 5/7225 600/323 |
| 2015/0062078 A1 | 3/2015 | Christman et al. | |
| 2016/0249864 A1* | 9/2016 | Kang | A61B 5/02055 340/870.07 |
| 2016/0270708 A1* | 9/2016 | Tateda | A61B 5/14552 |
| 2016/0278704 A1* | 9/2016 | Park | A61B 5/02 |
| 2016/0360971 A1 | 12/2016 | Gross et al. | |
| 2017/0143277 A1 | 5/2017 | Lisogurski | |
| 2017/0181680 A1 | 6/2017 | Baek et al. | |
| 2017/0284865 A1 | 10/2017 | Metrani | |
| 2019/0083034 A1 | 3/2019 | Shim et al. | |
| 2021/0038168 A1* | 2/2021 | Sudo | A61B 5/6843 |

FOREIGN PATENT DOCUMENTS

| | | |
|---|---|---|
| KR | 1020170092374 | 8/2017 |
| KR | 1020170123209 | 11/2017 |

OTHER PUBLICATIONS

European Search Report dated Jan. 4, 2022 issued in counterpart application No. 20763444.5-1113, 8 pages.
European Search Report dated Sep. 4, 2023 issued in counterpart application No. 20763444.5-1113, 7 pages.

* cited by examiner

ELECTRONIC DEVICE FOR MEASURING BIOMETRIC INFORMATION AND METHOD FOR OPERATING THE SAME

CROSS-REFERENCE TO RELATED APPLICATION(S)

This application is based on and claims priority under 35 U.S.C. § 119 to Korean Patent Application No. 10-2019-0021703, filed on Feb. 25, 2019, in the Korean Intellectual Property Office, the disclosure of which is incorporated by reference herein in its entirety.

BACKGROUND

1. Field

The disclosure relates to an electronic device for measuring biometric information and a method for operating the same.

2. Description of Related Art

In recent years, electronic devices including a sensor that may measure biometric information of a user have been developed. A user may measure information related to the body of the user by using an electronic device and may recognize the state of the body.

The electronic device may measure various pieces of biometric information, such as a heart rate, an oxygen saturation, a stress level, and a blood pressure of a user, by using a sensor. For example, the electronic device may sense biometric information at a portion of the body of the user by using the sensor. The electronic device may measure various pieces of biometric information on the user by using sensing information acquired through the sensor.

The electronic device may measure the oxygen saturation in blood by using a photoplethysmogram (PPG) acquired through the sensor when the biometric information, such as an oxygen saturation, is measured. Various methods for measuring an oxygen saturation are known and, generally, a method of using ratios of direct current (DC) components and alternating current (AC) components of infrared ray signals and red light signals is used. In a process of acquiring a PPG signal through a sensor, pressure applied to the body of a user may be generated by a sensor contact surface as a portion of the body of the user and the sensor contact each other. Then, a PPG signal acquired through the sensor may be distorted by the pressure applied to the body due to the sensor contact surface. Accordingly, in order to minimize an error of the oxygen saturation, the pressure applied to the body due to the sensor contact surface should be within a predetermined range or less.

Conventionally, when oxygen saturation is measured by using ratios of DC components and AC components of an infrared ray signal and a red light signal, distortion of a PPG signal due to pressure applied to a body by a sensor cannot be identified. That is, the conventional electronic device cannot accurately measure biometric information because the conventional electronic device cannot identify distortion of a PPG signal due to pressure applied to the body of the user by the sensor (or the sensor contact surface).

SUMMARY

An aspect of the disclosure provides an electronic device that can identify distortion of a PPG signal due to pressure applied to the body of a user by a sensor (or a sensor contact surface) when biometric information is measured, and a method for operating the same.

In accordance with an aspect of the disclosure, an electronic device is provided. The electronic device includes a housing, a touchscreen display viewable through a first part of the housing, a PPG sensor exposed through a second part of the housing, a processor disposed in the housing and operatively connected to the touchscreen display and the PPG sensor, and a memory disposed in the housing and operatively connected to the processor, wherein the memory is configured to store instructions that, when executed, are configured to cause the processor to receive first data from the PPG sensor, generate second data by band-pass filtering the first data, generate oxygen saturation data based at least some of the second data, select a first portion related to a first period of time from the second data, and display, on the touchscreen display, a graphical user interface including information related to the oxygen saturation data except for data corresponding to the first portion from the graphical user interface.

In accordance with another aspect of the disclosure, a method for operating an electronic device is provided. The method includes receiving first data from a PPG sensor of the electronic device, generating second data by band-pass filtering the first data, generating oxygen saturation data based on at least some of the second data, selecting a first portion related to a first period of time from the second data, and displaying, on a touchscreen display, a graphical user interface including information related to the oxygen saturation data except for data corresponding to the first portion from the graphical user interface.

In accordance with another aspect of the disclosure, an electronic device is provided. The electronic device includes a PPG sensor, a processor operatively connected to the PPG sensor, and a memory operatively connected to the processor, and the memory is configured to store instructions that, when executed, are configured to cause the processor to acquire a PPG signal for a user from the PPG sensor, identify signal distortion of first data due to pressure applied to a body of a user by the PPG sensor, based on at least a portion of second data generated by band-pass filtering the first data corresponding to the PPG signal, and in response to identifying that there is no signal distortion of the first data, identify biometric information using the PPG signal.

BRIEF DESCRIPTION OF THE DRAWINGS

The above and other aspects, features, and advantages of certain embodiments of the present disclosure will be more apparent from the following detailed description taken in conjunction with the accompanying drawings, in which.

DETAILED DESCRIPTION

Figure 1:
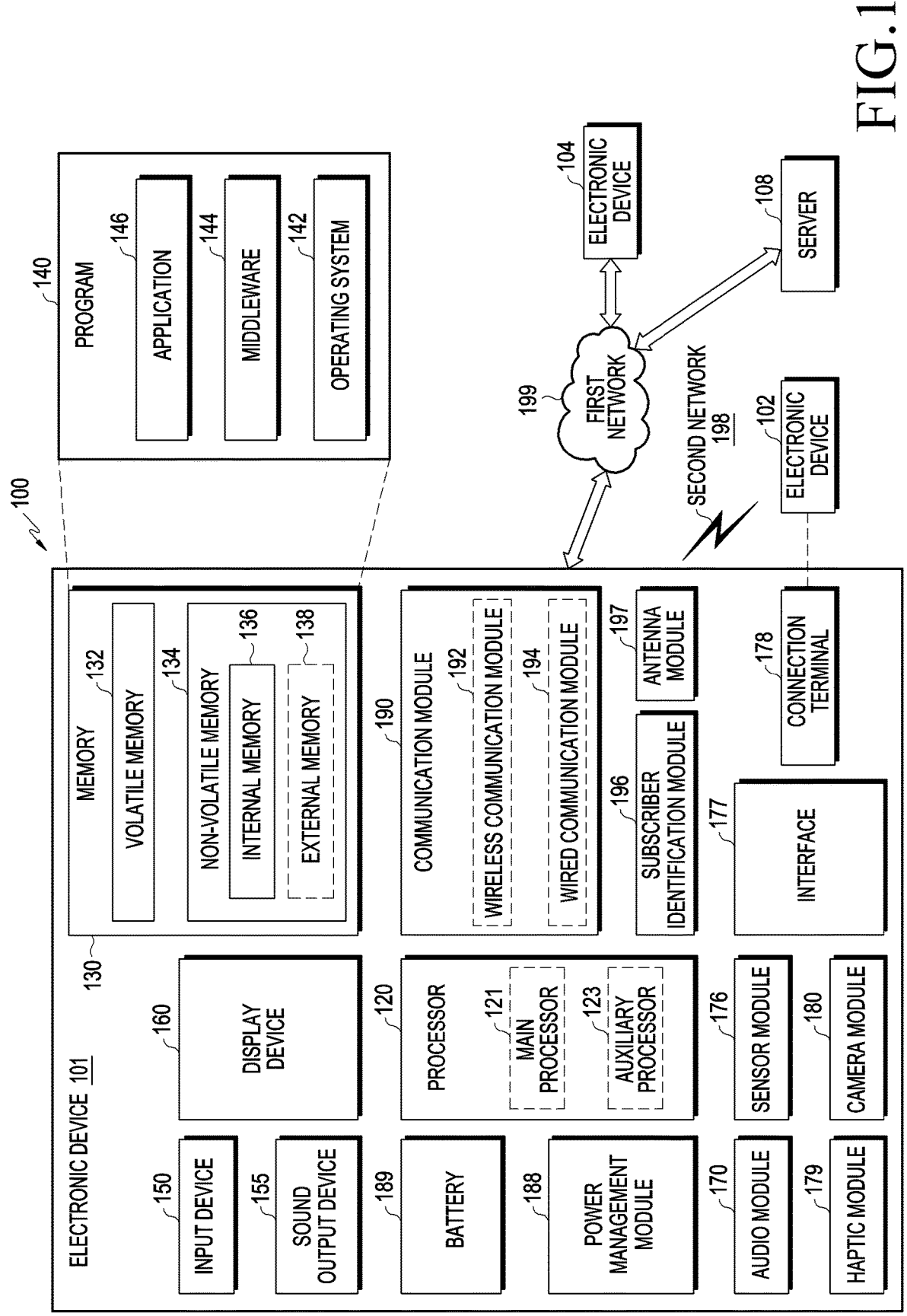
FIG. 1 is a block diagram of an electronic device in a network environment according to an embodiment.

FIG. 1 is a block diagram illustrating an electronic device 101 in a network environment 100 according to an embodiment. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an ISP or a CP) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by another component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or recording, and the receiver may be used for incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via the user's tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, ISPs, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more CPs that are operable independently from the processor 120. (e.g., the AP) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smart phone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

A method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 2:
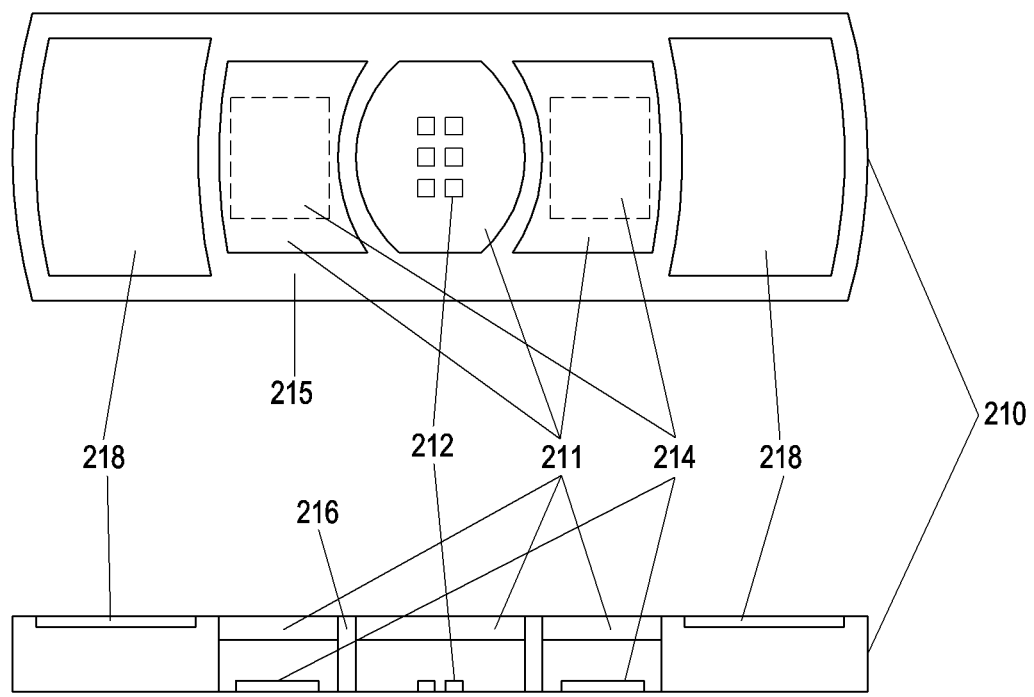
FIG. 2 is a block diagram of a top view and a side view of a sensor module according to an embodiment.

FIG. 2 is a block diagram of a top view and a side view of a sensor module 210 according to an embodiment.

Referring to FIG. 2, the sensor module 210 may include an optical window 211, a light emitting part 212, a light receiving part 214, an optical shield 215, an optical septum 216, and an electrode part 218.

The sensor module 210 may be implemented in a manner that is the same as, or similar to, that of the sensor module 176 of FIG. 1. The sensor module 210 may sense or acquire a signal related to a biometry or health of a user from at least a portion of the body of the user. The sensor module 210 may sense a signal related to at least one of a bioelectric impedance analysis (BIA), an electrocardiogram (ECG), a galvanic skin response (GSR), an electromyography (EMG), an electroencephalogram (EEG), and electrooculogram (EOG) of a user. The sensor module 210 may sense a signal related to at least one of a heart rate, an oxygen saturation, stress, and blood pressure of the user.

The biometric information that may be measured by using the sensor module 210 is simply illustrative, and the present disclosure is not limited thereto but may be implemented in various forms.

The sensing module 210 may be exposed to the outside through at least a portion of a housing of an electronic device (e.g., the electronic device 101 of FIG. 1).

The optical window 211 may cover the light emitting part 212 and the light receiving part 214. Light (or an optical signal) output from the light emitting part 212 may be output to the outside through the optical window 211. Light (or an optical signal) input from the outside may be input to the light receiving part 214 through the optical window 211. For example, the optical window 211 may be implemented by a transparent material (e.g., glass or plastic).

The light emitting part 212 may output light (or an optical signal) to the outside. For example, the light emitting part 212 may output light to skin of the user. For example, the light emitting part 212 may output at least one of an infrared ray, red light, green light, and/or blue light. For example, the light emitting part 212 may include at least one of a spectrometer, a vertical cavity surface emitting laser (VCSEL), a light emitting diode (LED), a white LED, and a white laser.

The light receiving part 214 may receive light (or an optical signal) input from the outside. For example, the light receiving part 214 may receive, among the light output from the light emitting part 212, at least a portion of light (or an optical signal) reflected from a body tissue (e.g., skin, a skin tissue, a fatty layer, a vein, an artery, and/or a capillary blood vessel) of the user. The light receiving part 214 may output a signal corresponding to the received light. For example, the light receiving part 214 may include at least one of an avalanche photodiode (APD), a single photon avalanche diode (SPAD), a photodiode, a photomultiplier tube (PMT), a charge coupled device (CCD), a complementary metal oxide semiconductor (CMOS) array, and spectrometer.

The light emitting part 212 and the light receiving part 214 may be exposed to the outside through at least a portion of a housing of the electronic device 101.

Although FIG. 2 designates and illustrates the numbers, the shapes, the sizes, and the locations of the light emitting part 212 (or the elements included in the light emitting part 212) and the light receiving part 214 (or the elements included in the light receiving part 214) for convenience of description, the numbers, the shapes, the sizes, and the locations of the light emitting part 212 and the light receiving part 214 are not limited thereto but may be implemented in various forms.

The optical shield 215 may interrupt light (or an optical signal) input from the outside. For example, the optical shield 215 may include a material that may interrupt light input from the outside. The shape and the size of the optical shield 215 may be determined variously.

The optical septum 216 may interrupt movement of light between the light emitting part 212 and the light receiving part 214. The optical septum 216 may be located between the light emitting part 212 and the light receiving part 214. For example, the optical septum 216 may interrupt the light output from the light emitting part 212 from being directly input to the light receiving part 214.

The electrode part 218 may be implemented by a conductive member through which a current flows. For example, the electrode part 218 may be implemented by a conductive member (e.g., stainless steel, silver, and/or gold) of a low resistance. The electrode part 218 may include a plurality of electrodes, and the shapes and the sizes of the plurality of electrodes may be determined variously.

The electrode part 218 may be exposed to the outside through at least a portion of the housing of the electronic device.

Although FIG. 2 designates and illustrates the number, the shape, the size, and the location of the electrode part 218 (or the electrodes included in the electrode part 218) for convenience of description, the number, the shape, the size, and the location of the electrode part 218 are not limited thereto but may be implemented in various forms.

The electrode part 218 may be electrically connected to at least one biometric sensor 176 included in the electronic device 101 and may be used to acquire biometric information, body information, or health information of the user. The electrode part 218 may be used to measure a BIA through the biometric sensor included in the electronic device 101 and measure a body fat percentage of the user, may be used to measure an ECG and measure a cardiogram of the user, and may be used to measure a GSR and measure (or calculate) the skin resistance and/or the skin hydration of the user. The electronic device 101 may measure the blood pressure of a pulse wave velocity (PWV) manner by using a PPG signal acquired through the electrode part 218 and the light receiving part 214. The biometric information that may be measured by using the electrode part 218 is simply illustrative, but the present disclosure is not limited thereto but may be implemented in various forms.

The electrode part 218 may be electrically connected to a charging circuit included in the electronic device 101. The charging circuit may refer to a circuit including a power management module 188 and/or a battery 189. The charging circuit may refer to a circuit that electrically connects at least one element of the electronic device 101 and the power management module 188 or the battery 189.

Although FIG. 2 illustrates that the light emitting part 212, the light receiving part 214, and the electrode part 218 are provided on the same plane of the sensor module 210, the present disclosure is not limited thereto. For example, the light emitting part 212 and the light receiving part 214 may be provided on a first surface of the electronic device 101, and the electrode part 218 may be provided on a second surface that is different from the first surface of the electronic device 101.

Figure 3:
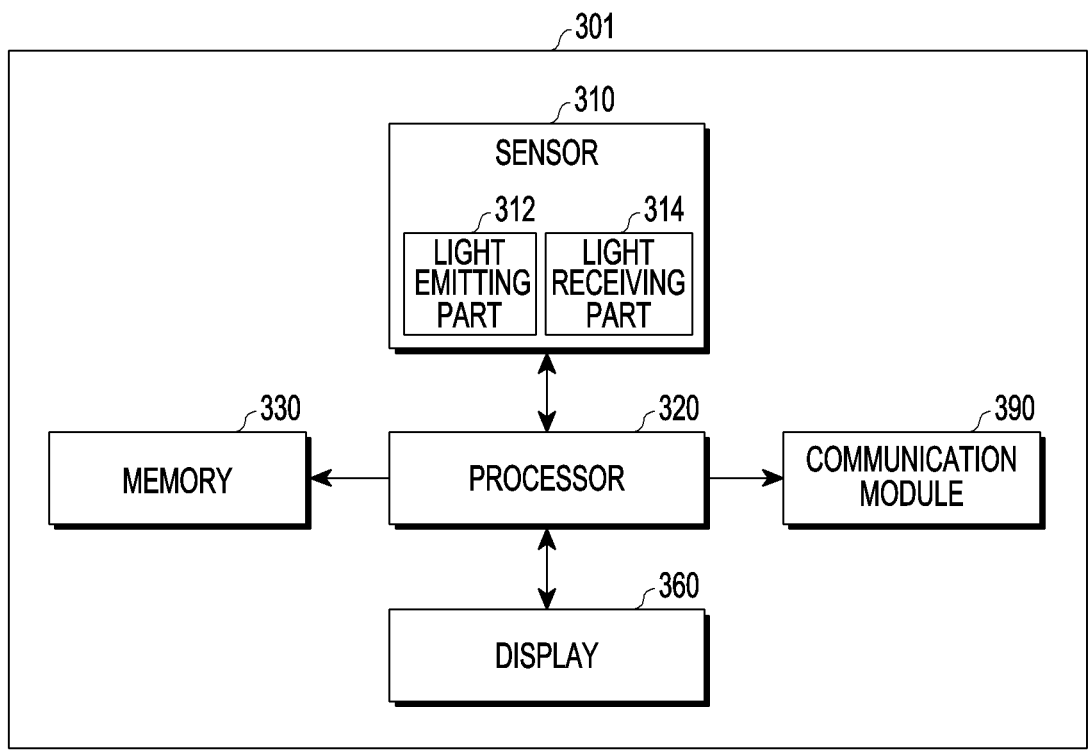
FIG. 3 is a block diagram of an electronic device according to an embodiment.

FIG. 3 is a block diagram of an electronic device 301 according to an embodiment.

Referring to FIG. 3, the electronic device 301 may include a sensor 310, a processor 320, a memory 330, a display 360, and a communication module 390. For example, the electronic device 301 may be implemented in a manner that is the same as or similar to the electronic device 101 of FIG.

1. For example, the electronic device 301 may include a wearable device or a smart watch.

The sensor 310 may acquire a biometric signal of a user. The sensor 310 may transmit the acquired biometric signal to the processor 320. For example, the sensor 310 may include a PPG sensor. The biometric signal may include a PPG signal. For example, the sensor 310 may be implemented in a manner that is the same as or similar to that of the sensor module 210 described above with reference to FIG. 2.

The sensor 310 may include a light emitting part 312 and a light receiving part 314. For example, the light emitting part 312 may output light (or an optical signal) to skin of the user. For example, the light emitting part 312 may output at least one of an infrared ray, red light, green light, and/or blue light (or an optical signal) according to the biometric information that is to be measured. For example, the light emitting part 312 may output at least one of an infrared ray signal and a red light signal when an oxygen saturation is measured.

For example, the light receiving part 314 may receive, among the light (or an optical signal) output from the light emitting part 312, at least a portion of light (or an optical signal) reflected from a body tissue (e.g., skin, skin tissue, a fatty layer, a vein, an artery, and/or a capillary blood vessel) of the user. The light receiving part 314 may output a biometric signal (e.g., a PPG signal) corresponding to the received light. For example, the light receiving part 314 may include a photodiode.

The sensor 310 may be exposed through a certain part of the housing of the electronic device 301. For example, the sensor 310 may contact a portion of the body of the user through the exposed part.

The processor 320 may control an overall operation of the electronic device 301. For example, the processor 320 may be implemented in a manner that is the same as or similar to the processor 120 of FIG. 1.

The processor 320 may acquire a biometric signal (e.g., a PPG signal) for the user through the sensor 310. The processor 320 may band-pass filter a certain frequency band for first data corresponding to the biometric signal (e.g., the PPG signal). The processor 320 may generate second data by band-pass filtering the first data. The processor 320 may identify signal distortion of the first data corresponding to the biometric signal based on the second data.

The processor 320 may identify signal distortion of the first data generated due to pressure applied to the body of the user by the sensor 310, based on a waveform of a signal included in the second data. The pressure applied to the body of the user by the sensor 310 may refer to pressure applied to the body of the user in contact with a contact surface of the sensor 310. For example, the pressure applied to the body of the user by the sensor 310 may include pressure applied to a finger part of the user in contact with the contact surface of the sensor 310.

The degrees of expansion and contraction of a blood vessel vary according to the pressure generated in the interior of the body due to the contact surface of the sensor 310, and the DC and the AC values of the PPG signal may be remarkably changed as compared with general values. The signal distortion of the first data (or the distortion of the PPG signal) may refer to a state, in which a signal distorted by the DC and the AC values changed according to the pressure applied to the body of the user in contact with the contact surface of the sensor 310, is generated.

The processor 320 may identify signal distortion of the first data due to the pressure applied to the body of the user by the sensor 310, by comparing a ratio of a positive maximum amplitude value and a negative maximum amplitude of the signal included in the second data with a preset threshold value.

The phrase "no signal distortion" may indicate that there is no signal distortion or there is signal distortion within a range, the error of which may be ignored. The phrase "no pressure" may indicate that there is no pressure that is higher than a normal range (e.g., the range for no distortion) for measuring biometric information.

The first data may be a biometric signal (e.g., a PPG signal) acquired through a sensor. The second data may be a signal generated by band-pass filtering the first data of a certain frequency band.

The processor 320 may measure or identify biometric information by using the first data if it is identified that there is no signal distortion of the first data. For example, the biometric information may refer to information related to the biometry or health that may be measured by using a PPG signal and may include information on a heart rate, an oxygen saturation, stress, and/or blood pressure.

The processor 320 may neither measure nor identify biometric information by using the first data if it is identified that there is signal distortion of the first data. The processor 320 may measure or identify biometric information while excluding the first data having signal distortion if it is identified that there is signal distortion of the first data. Then, the processor 320 may provide the measured biometric information while excluding the first data having signal distortion. Further, the processor 320 may provide a notification that indicates that there is signal distortion by pressure while providing biometric information based on the first data having signal distortion.

The processor 320 may receive the first data from the sensor 310, generate the second data by performing band-pass filtering corresponding to a certain frequency band on the first data, and may generate biometric information based on at least a portion of the second data. The processor 320 may select a part related to a certain period of time from the second data after generating the biometric information, analyze the selected part, and identify signal distortion (due to pressure applied to a body due to the contact surface of the sensor 310) of the part related to the certain period of time. For example, the processor 320 may identify signal distortion due to the pressure applied to a body by the sensor 310 (or the contact surface of the sensor 310) by comparing a ratio of a positive maximum amplitude and a negative maximum amplitude of the waveform of the signal included in the second data with a threshold value.

The processor 320 may provide a graphic user interface including the biometric information. Then, the processor 320 may exclude a part in which signal distortion is generated due to pressure applied to a body with the sensor 310. For example, the processor 320 may display a graphic user interface including information related to oxygen saturation data on the display 360 and may exclude the oxygen saturation data corresponding to the part in which signal distortion is generated from the graphic user interface. Further, the processor 320 may store, in the memory 330, the biometric information data except for the oxygen saturation data corresponding to the part in which signal distortion is generated. The processor 320 may distinguish the part corresponding to the part in which signal distortion is generated (e.g., by using identification information) and store the oxygen saturation data in the memory 330.

The memory 330 may store data and/or instructions of the electronic device 301. The memory 330 may be implemented in a manner that is the same as or similar to the memory 130 of FIG. 1. For example, the memory 330 may store the biometric information measured or identified by the processor 320.

The display 360 may display data or information of the electronic device 301. The display 360 may display the biometric information data (or the graphic user interface including the biometric information data) measured or identified by the processor 320.

The display 360 may include a touchscreen (or a touchscreen display). The display 360 may be viewed through the first part of the housing of the electronic device 301. For example, the first part of the electronic device 301 may be a part that is different from the part (e.g., the second part) through which the sensor 310 is exposed. Further, the first part of the electronic device 301 may be a part that is opposite to the part (e.g., the second part) through which the sensor 310 is exposed.

The communication module 390 may transmit data to an external electronic device or may receive data from an external electronic device.

The operation performed by the electronic device 301, which is described below in greater detail, may be an operation by the processor 320 included in the electronic device 301.

Figure 4:
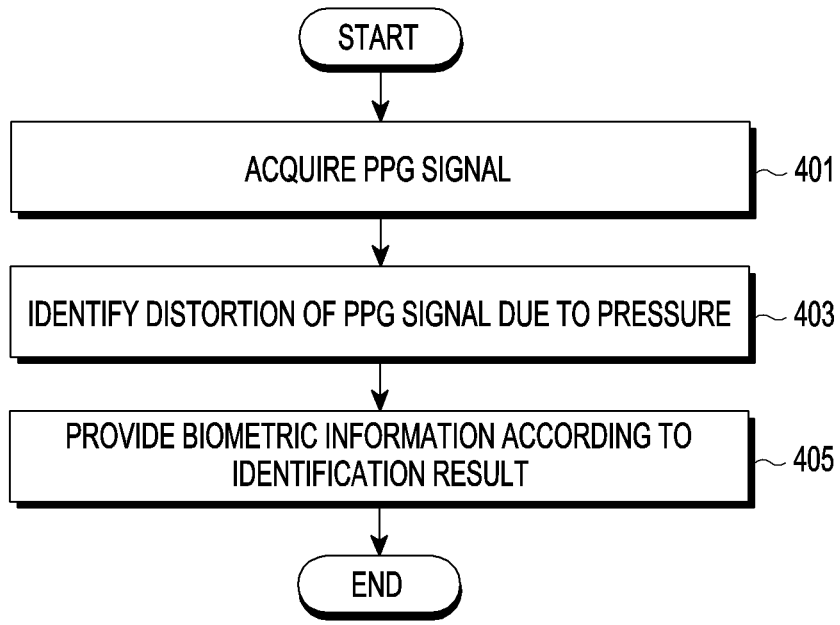
FIG. 4 is a flowchart of a method of an electronic device according to an embodiment.

FIG. 4 is a flowchart 400 of a method of an electronic device according to an embodiment.

Referring to FIG. 4, in step 401, an electronic device may acquire a PPG signal through a sensor.

In step 403, the electronic device 301 may identify distortion of a PPG signal due to pressure applied to a body by the sensor 310. For example, the electronic device 301 may band-pass filter a PPG signal and may identify distortion of the band-pass filtered PPG signal due to pressure by comparing a ratio of a positive maximum amplitude and a negative maximum amplitude of the PPG signal with a threshold value. That is, the positive maximum amplitude and the negative maximum amplitude may refer to maximum amplitudes having signs after the PPG signal is band-pass filtered. The threshold value may be a predetermined value or may be set automatically or manually.

In step 405, the electronic device 301 may measure and identify biometric information by using the PPG signal according to the identification result and may provide the measured and identified biometric information. For example, the electronic device 301 may not provide biometric information if it is identified that there is distortion of the PPG signal due to pressure. The electronic device 301 may inform that the biometric information may be information distorted by pressure while providing the biometric information. Further, the electronic device 301 may normally provide the biometric information by using a PPG signal if distortion of the PPG signal due to pressure is not identified.

Figure 5:
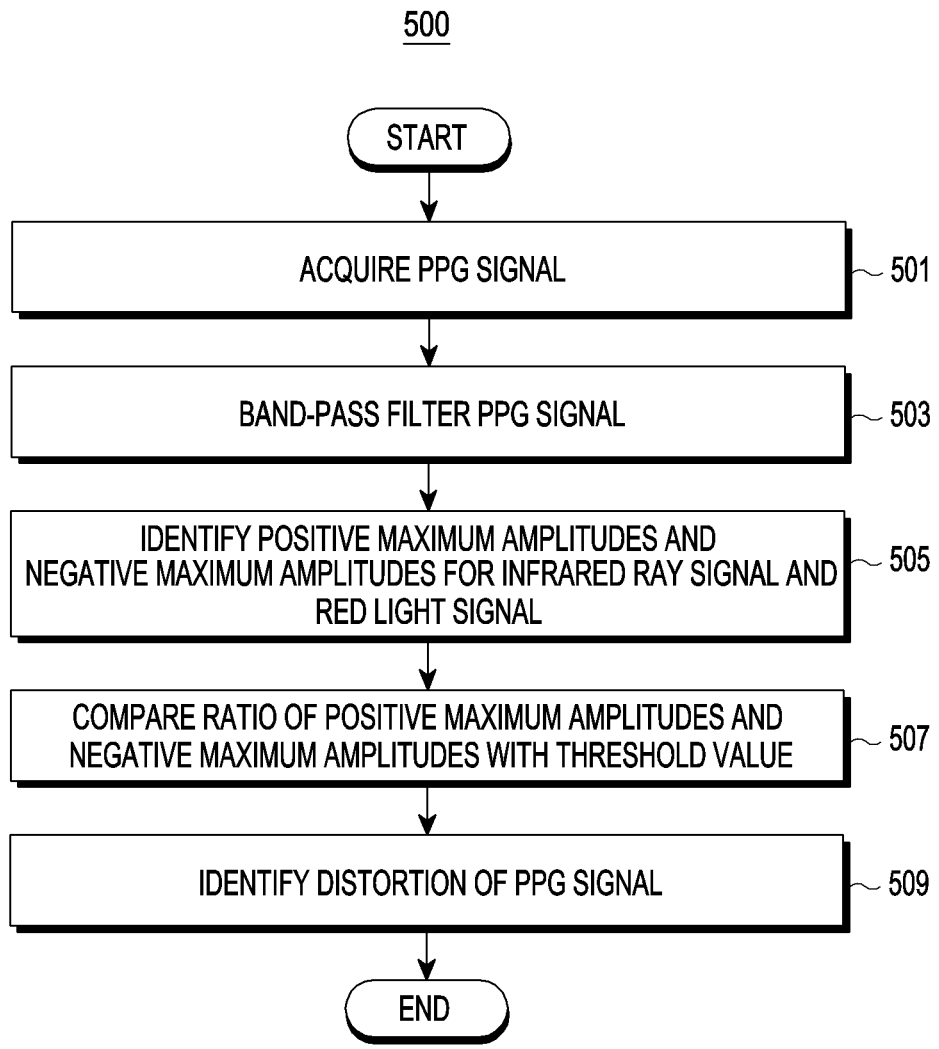
FIG. 5 is a flowchart of a method of an electronic device identifying distortion of a PPG signal according to an embodiment.

FIG. 5 is a flowchart 500 of a method of an electronic device identifying distortion of a PPG signal according to an embodiment.

Figure 6A:
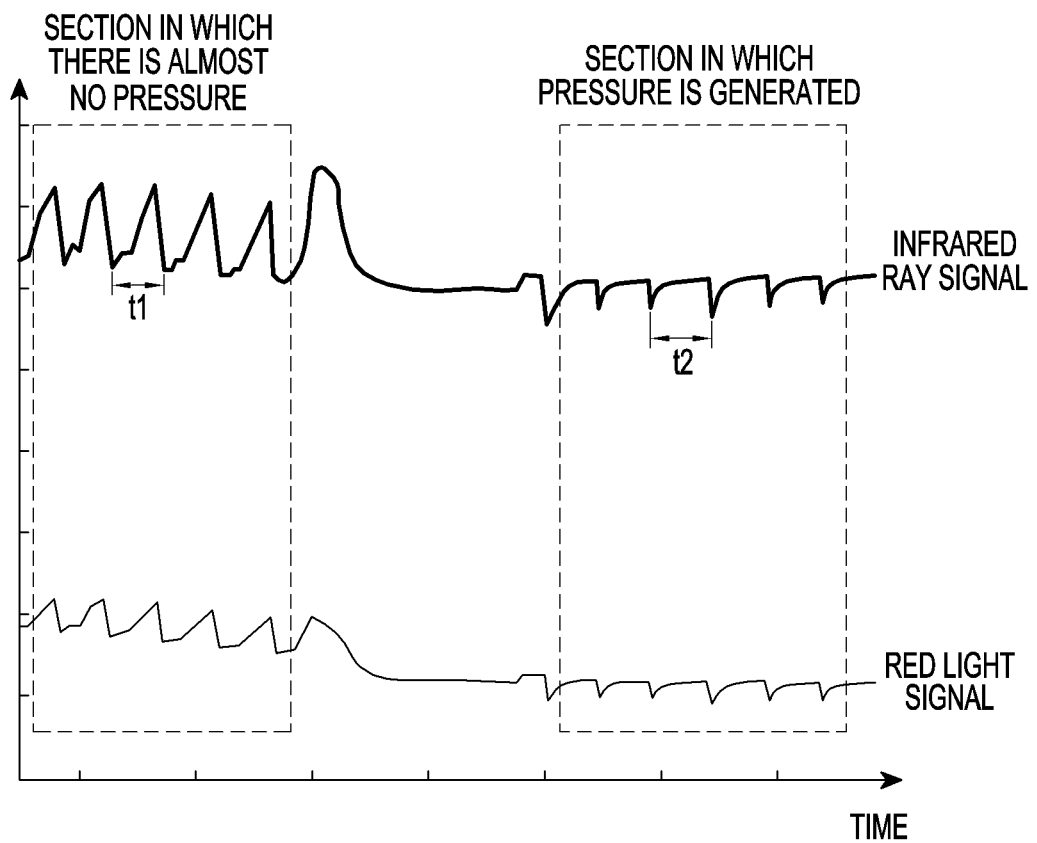
FIG. 6A is a graph of an electronic device identifying distortion of a PPG signal according to an embodiment.
Figure 6B:
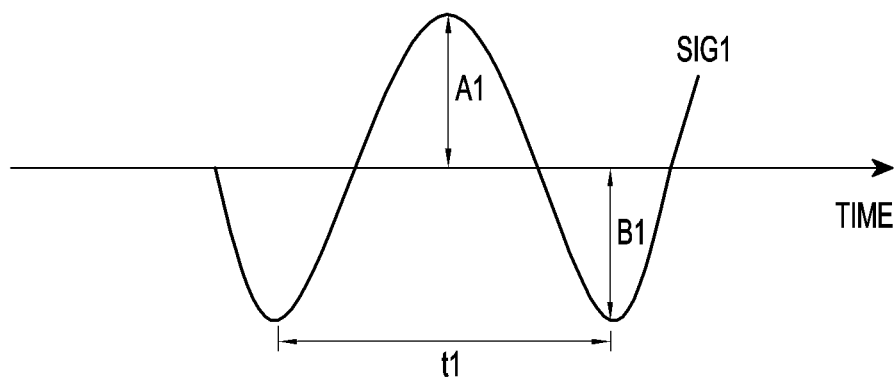
FIG. 6B is a graph of an electronic device identifying distortion of a PPG signal according to an embodiment.
Figure 6C:
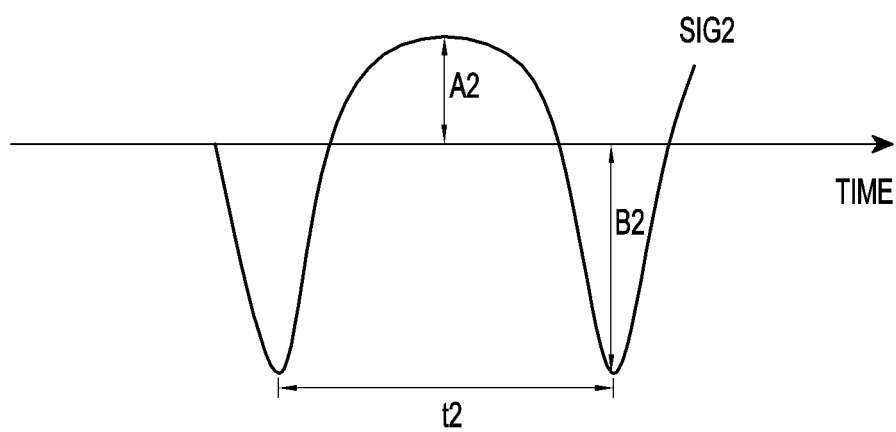
FIG. 6C is a graph of an electronic device identifying distortion of a PPG signal according to an embodiment.

FIG. 6A is a graph 601 of an electronic device identifying distortion of a PPG signal according to an embodiment, FIG. 6B is a graph 602 of an electronic device identifying distortion of a PPG signal according to an embodiment, and FIG. 6C is a graph 603 of an electronic device identifying distortion of a PPG signal according to an embodiment. The operation of FIG. 5 of identifying distortion of a PPG signal is described below with reference to the graphs of FIGS. 6A to 6C.

Referring to FIG. 5, in step 501, an electronic device may acquire a PPG signal through a sensor.

Referring to FIG. 6A, the PPG signal may include an infrared ray signal and a red light signal. For example, the PPG signal may include a signal (e.g., an infrared ray signal and a red light signal) acquired in a section in which pressure is not generated in the sensor 310 and a signal acquired in a section in which pressure is generated in the sensor 310. If pressure is generated in the sensor 310, distortion of a signal (or a signal waveform) may be generated as compared with the signal corresponding to the case in which pressure is not generated.

In step 503, the electronic device 301 may band-pass filter the PPG signal for a certain frequency. For example, the band-pass filter for performing band-pass filtering may include a finite impulse response (FIR) filter. For example, the pass band of the band-pass filter for performing band-pass filtering may be determined in consideration of a range of the frequency of heartbeats of a person. For example, the pass band of the band-pass filter may be determined to be a frequency range of 0.5 Hz to 4.0 Hz. For example, the power of the band-pass filter may be designated to be 150. The number of filter coefficients may be the power of the filter plus one, and if the power of the band-pass filter is 150, the number of the filter coefficients may be 151. For example, the n-th output (y(n)) of the FIR band-pass filter may be determined by the power (N) of the filter, the coefficients (h(0) to h(N)) of the filter, and input data (x), and may be determined in Equation (1) as follows.

$$y(n) = \sum_{k=0}^{N} h(k)^* x(n-k) \tag{1}$$

In step 505, the electronic device 301 may identify positive maximum amplitudes and negative maximum amplitudes of the infrared light signal and the red light signal included in the PPG signal.

Referring to FIG. 6B, the electronic device 301 may acquire a first signal (SIG1) by band-pass filtering the infrared ray signal (or the red light signal) in section t1. For example, section t1 may be a section in which no pressure is generated in the sensor 310 or almost no pressure is generated.

The electronic device 301 may identify the positive maximum amplitude (A1) and the negative maximum amplitude (B1) of the first signal (SIG1) for the infrared ray signal (or the red light signal). For example, the positive maximum amplitude (A1) and the negative maximum amplitude (B1) of the first signal (SIG1) may be values that are the same or similar.

Referring to FIG. 6C, the electronic device 301 may acquire a second signal (SIG2) by band-pass filtering the infrared ray signal (or the red light signal) in section t2. For example, section t2 may be a section in which pressure is generated in the sensor 310.

The electronic device 301 may identify the positive maximum amplitude (A2) and the negative maximum amplitude (B2) of the second signal (SIG2) for the infrared ray signal (or the red light signal). For example, the positive maximum amplitude (A2) and the negative maximum amplitude (B2) of the second signal (SIG2) may be different values.

In step 507, the electronic device 301 may, after identifying the positive maximum amplitudes and the negative maximum amplitudes of the infrared light signal and the red light signal included in the PPG signal, compare the ratios of the identified positive maximum amplitudes and negative maximum amplitudes of the infrared ray signal and the red light signal with threshold values. For example, the electronic device 301 may compare an A1/|B1| value of the infrared ray signal with a first threshold value (a threshold value for the infrared ray signal) and may compare an A1/|B1| value of the red light signal with a second threshold value (a threshold value for the red light signal). The electronic device 301 may compare an A2/|B2| value of the infrared ray signal with the first threshold value and may compare an A2/|B2| value of the red light signal with the second threshold value. For example, the first threshold value and the second threshold value may be predetermined values and may be automatically determined by the processor 320 or manually determined through an input of the user.

In step 509, the electronic device 301 may identify distortion of the PPG signal. For example, the electronic device 301 may identify distortion of the PPG signal according to a result obtained by comparing the ratios of the identified positive maximum amplitudes and the negative maximum amplitudes of the infrared ray signal and the red light signal with the corresponding threshold values. For example, the electronic device 301 may, when the A1 value and the |B1| value for the infrared light signal (or the red light signal) are the same or almost the same, because the A1/|B1| value is a value that is approximate to 1, determine that there is no signal distortion. The electronic device 301 may, when the A2 value and the |B2| value for the infrared light signal (or the red light signal) are different, because the A2/|B2| value is a value that is not approximate to 1, determine that there is signal distortion. Then, the electronic device 301 may determine the degree of signal distortion according to the A2/|B2| value.

The electronic device 301 may determine that signal distortion is generated by the pressure applied to the sensor 310 if the A2/|B2| values for the infrared ray signal and the red light signal are less than the threshold values as in the infrared ray signal and the red light signal in section t2. In contrast, the electronic device 301 may determine that no signal distortion is generated by the pressure applied to the sensor 310 if the A2/|B2| values for the infrared ray signal and the red light signal are not less than the threshold values as in the infrared ray signal and the red light signal in section t1.

Figure 7A:
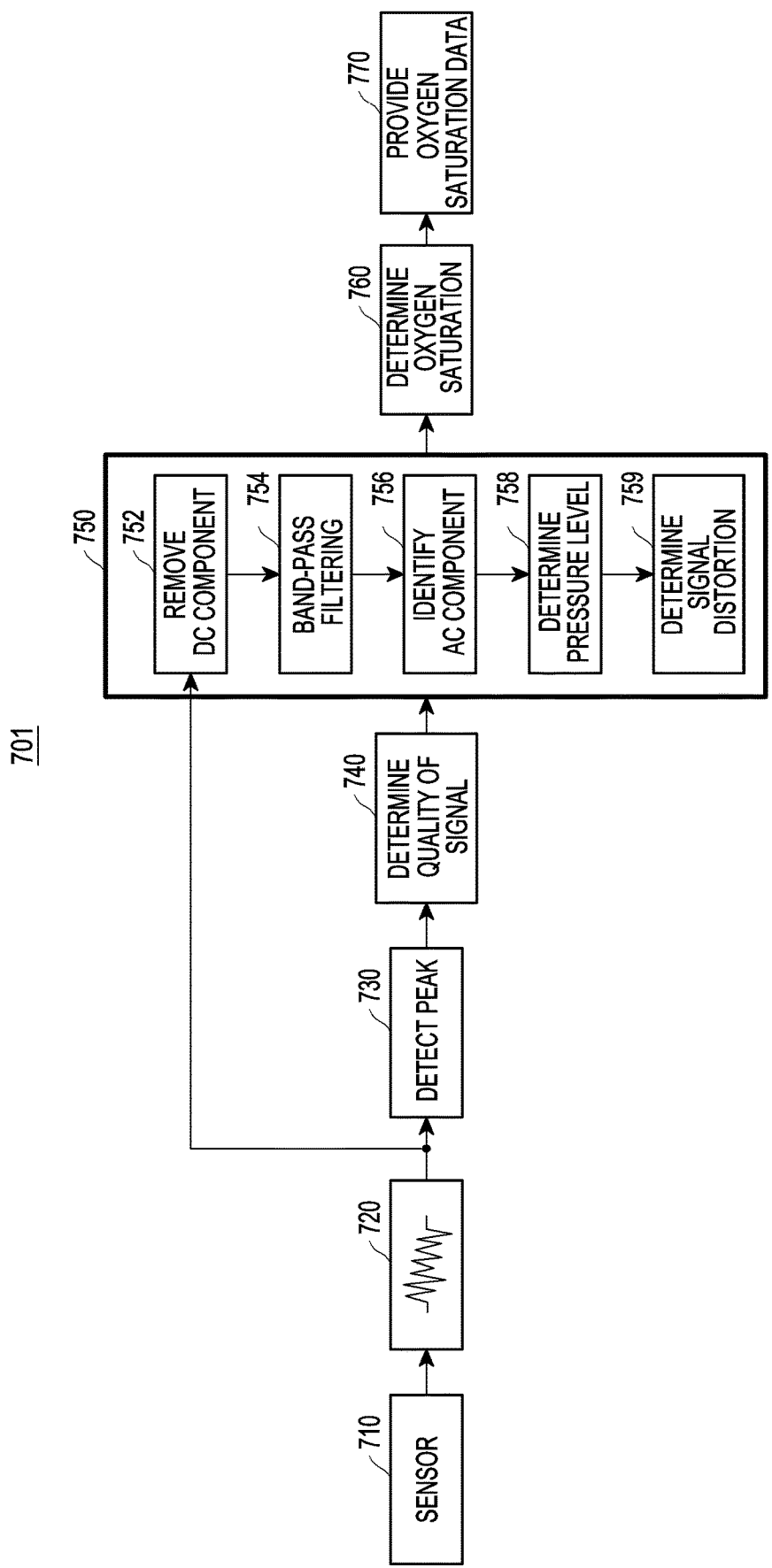
FIG. 7A is a block diagram of a method of an electronic device providing biometric information according to an embodiment.
Figure 7B:
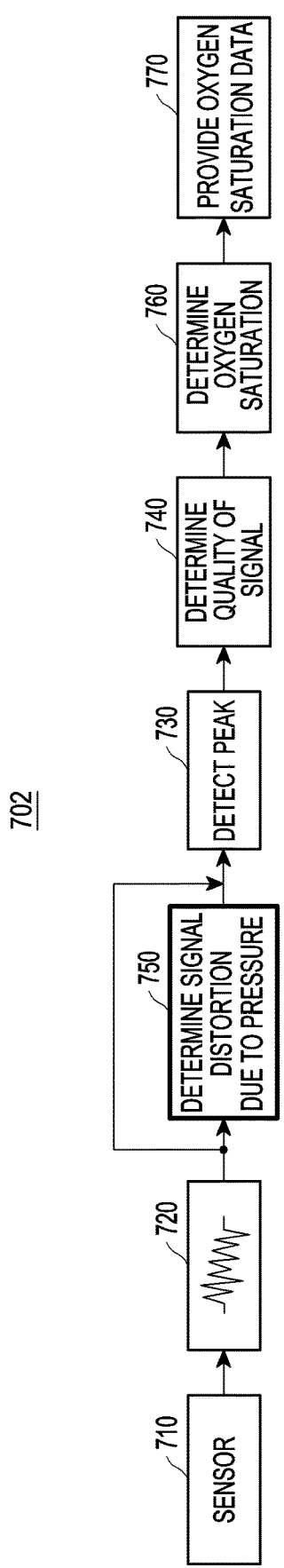
FIG. 7B is a block diagram of a method of an electronic device providing biometric information according to an embodiment.
Figure 7C:
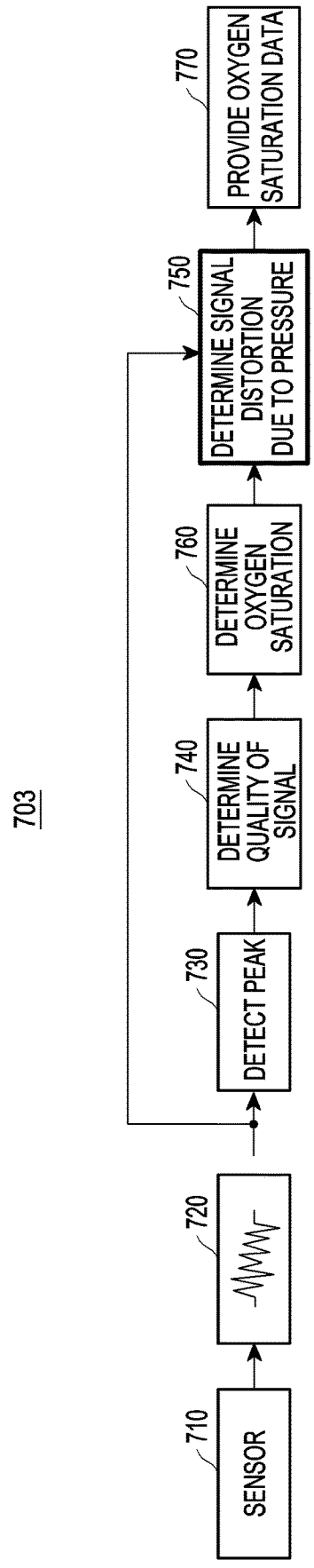
FIG. 7C is a block diagram of a method of an electronic device providing biometric information according to an embodiment.

FIG. 7A is a block diagram 701 illustrating a method of an electronic device providing biometric information according to an embodiment, FIG. 7B is a block diagram 702 of a method of an electronic device providing biometric information according to an embodiment, and FIG. 7C is a block diagram 703 of a method of an electronic device providing biometric information according to an embodiment.

Referring to FIG. 7A, in step 710, a sensor of an electronic device may contact a portion of a body of a user.

In step 720, an electronic device 301 may output an infrared ray signal (an IR signal) or a red light signal to a portion of the body of the user in contact with the sensor 310 and may acquire the infrared light signal and the red light signal reflected from the portion of the body of the user. That is, the electronic device 301 may acquire the infrared light signal and the red light signal through the sensor 310.

In step 730, the electronic device 301 may identify peaks (or peak values) of the infrared light signal and the red light signal. For example, the electronic device 301 may identify (or estimate) the peaks (or peak values) of the signals generated for the infrared light signal and the red light signal by heartbeats.

In step 740, the electronic device 301 may determine the quality of a signal based on a similarity of periodicities or shapes of the infrared ray signal and the red light signal for one period or integer time sections of the one period with reference to the peak (or peaks) included in the infrared ray signal and the red light signal. For example, the electronic device 301 may determine the quality of the signal by calculating change rates of the time intervals for the acquired sections, the change rates of the amplitudes of the signals for the sections and/or the correlation between the signals with the peaks acquired in the sections that are adjacent to the peak included in the signal. The electronic device 301 may not be used for measuring biometric information (e.g., an oxygen saturation) for a signal in a section having a bad quality of a signal. That is, the electronic device 301 may measure biometric information (e.g., an oxygen saturation) for a signal in a section having a good quality of a signal.

In step 750, the electronic device 301 may identify or determine signal distortion due to pressure applied to the sensor 310. For example, the electronic device 301 may identify distortion of a signal by pressure for a signal in a section having an excellent quality of a signal, before the biometric information is measured.

In step 752, the electronic device 301 may remove a DC component of a PPG signal. For example, the electronic device 301 may acquire the DC component from an average value of the PPG signal or a primary infinite impulse response (IIR) filtering value and may remove the DC component. In step 754, the electronic device 301 may band-pass filter the PPG signal, from which the DC component has been removed. In step 756, the electronic device 301 may identify the AC component of the PPG signal from the output of the band-pass filtering. In step 758, the electronic device 301 may identify the ratio of the positive amplitude and the negative amplitude of the AC component of the PPG signal and may determine a pressure level applied to the sensor 310 by comparing the identified ratio with a certain threshold value. In step 759, the electronic device 301 may determine that the signal is distorted based on the determined pressure level. For example, the electronic device 301 may, when there is no pressure or the pressure level is lower than a certain value, determine that no signal distortion by pressure is generated.

In step 760, the electronic device 301 may determine or measure biometric information (e.g., an oxygen saturation). For example, the electronic device 301 may measure the biometric information by using a signal which has a good quality and in which there is no distortion of the signal by pressure. The electronic device 301 may calculate AC and DC components for the peaks of the infrared ray signal and the red light signal and may calculate an R value based on the calculated values. That is, the electronic device 301, as in Equation (2) below, may calculate an R value by using an AC component (REDAC) of the red light signal, a DC component (REDDC) of the red light signal, an AC component (IRAC) of the infrared ray signal, and a DC component (IRDC) of the infrared ray signal.

$$R = (REDAC/REDDC)/(IRAC/IRDC) \qquad (2)$$

The electronic device 301 may be modeled in a polynomial of the first or second degree for the R calculated in Equation (2) above and may measure biometric information (e.g., an oxygen saturation) by using the specified model.

For example, Equation (2) above may be applied only to the case in which the biometric information is an oxygen saturation. That is, when biometric information that is different from an oxygen saturation, an equation that is different from Equation (2) above may be applied. Then, when the biometric information that is different from the oxygen saturation is measured, an equation that is suitable for measuring the corresponding biometric information may be applied.

In step 770, the electronic device 301 may provide data for biometric information (e.g., an oxygen saturation). For example, the electronic device 301 may display the data for the biometric information (e.g., an oxygen saturation) on a display 360. Further, the electronic device 301 may store the data for the biometric information (e.g., an oxygen saturation) in a memory 30.

Referring to FIG. 7B, the electronic device 301 may, before detecting the peaks of the infrared ray signal and the red light signal acquired in step 720, identify or determine signal distortion due to pressure applied to the sensor 310 (in step 750). That is, the electronic device 301 may detect a peak value only for a signal in which distortion due to pressure is not generated and may determine the quality of the signal.

Referring to FIG. 7C, the electronic device 301 may, after measuring the biometric information (e.g., an oxygen saturation), identify or determine signal distortion by pressure applied to the sensor 310 (in step 750). That is, the electronic device 301 may, after determining the quality of the signal with reference to the detected peaks and measuring the biometric information (e.g., an oxygen saturation) of the signal having a good quality, determine generation of signal distortion by pressure. For example, the electronic device 301 may provide biometric information (e.g., an oxygen saturation) data and may exclude data for which signal distortion has been identified. Further, the electronic device 301 may provide biometric information (e.g., an oxygen saturation) data and may provide a notification (that informs that the corresponding data has an error due to pressure) on the data for which signal distortion has been identified.

Although FIGS. 7A to 7C illustrate only three cases in which the sequences of the operation (step 750) of determining signal distortion by pressure are implemented differently, the present disclosure is not limited thereto but may be implemented in various sequences.

Figure 8:
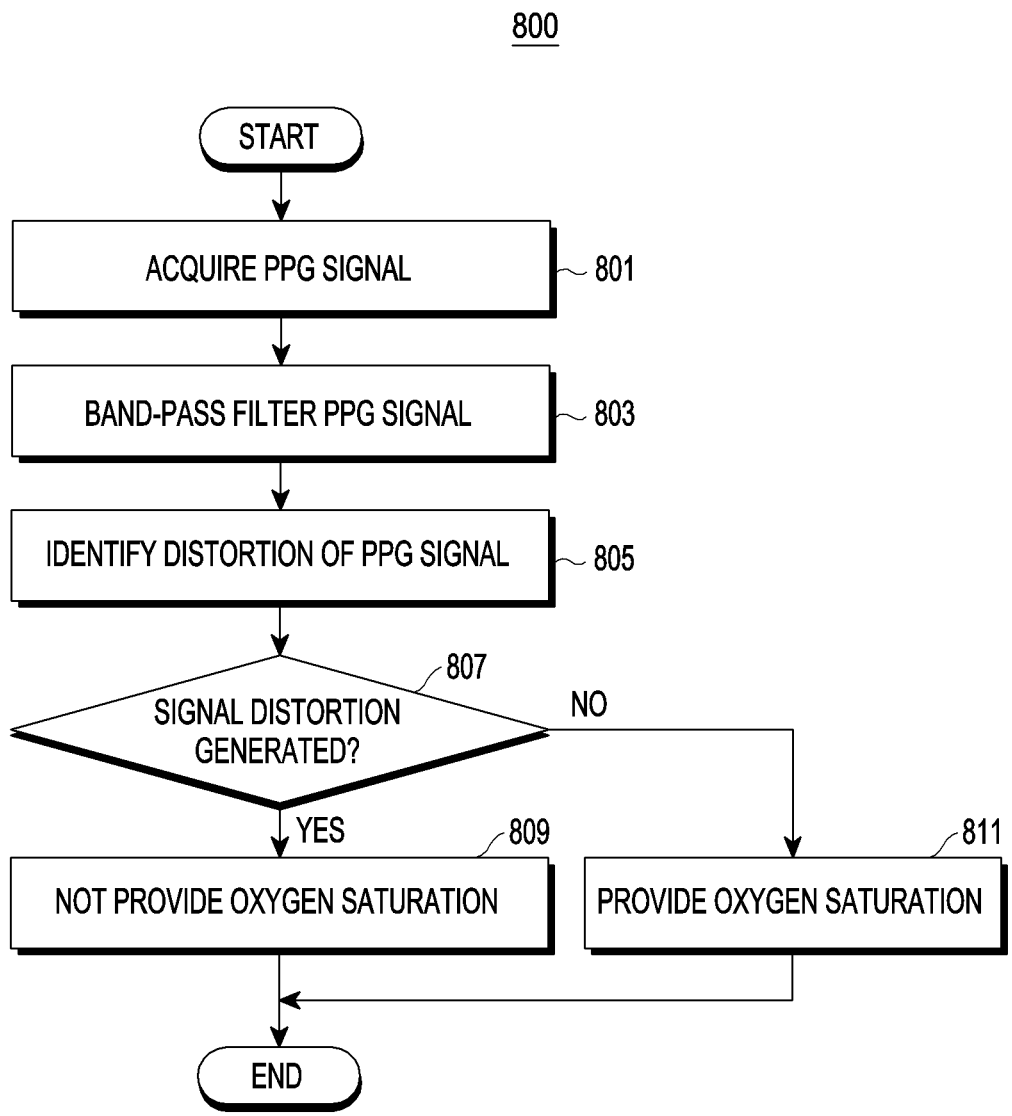
FIG. 8 is a flowchart of a method of an electronic device providing biometric information according to distortion of a PPG signal according to an embodiment.

FIG. 8 is a flowchart 800 is a flowchart of a method of an electronic device providing biometric information according to distortion of a PPG signal according to an embodiment.

Referring to FIG. 8, in step 801, an electronic device may acquire a PPG signal through a sensor 310. For example, the electronic device 301 may acquire the PPG signal for an infrared ray signal and a red light signal. For example, the electronic device 301 may acquire first data corresponding to the PPG signal.

In step 803, the electronic device 301 may band-pass filter the PPG signal for a certain frequency. The electronic device 301 may generate second data by band-pass filtering the first data.

In step 805, the electronic device 301 may analyze a waveform of a signal included in the second data and may identify distortion of a signal included in the second data due to pressure applied to the sensor.

If distortion of the signal included in the second data is identified (e.g., YES in step 807), in step 809, the electronic device 301 may not measure biometric information (e.g., an oxygen saturation) and may not provide the measured biometric information (e.g., an oxygen saturation). For example, the electronic device 301 may not measure an oxygen saturation by using the signal for which distortion has been identified, and may not provide information on the measured oxygen saturation even though the oxygen saturation is measured. Further, the electronic device 301 may provide information on the measured oxygen saturation and may inform that the corresponding information has an error.

If distortion of the signal included in the second data is not identified (e.g., NO in step 807), in step 811, the electronic device 301 may measure biometric information (e.g., an oxygen saturation) and may provide the measured biometric information (e.g., an oxygen saturation). For example, the electronic device 301 may measure an oxygen saturation by using a signal for which distortion has not been identified.

Figure 9:
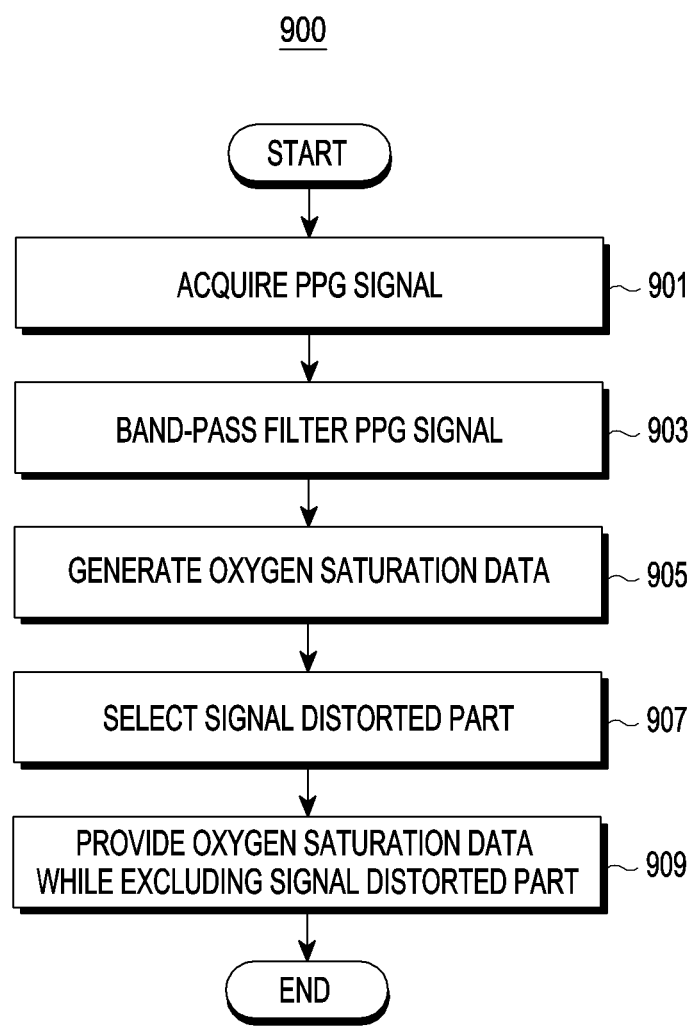
FIG. 9 is a flowchart of a method of an electronic device providing biometric information according to an embodiment.

FIG. 9 is a flowchart 900 of a method of an electronic device providing biometric information according to an embodiment.

Referring to FIG. 9, in step 901, an electronic device may acquire a PPG signal through a sensor 310. For example, the electronic device 301 may acquire PPG signals for an infrared ray signal and a red light signal. For example, the electronic device 301 may acquire first data corresponding to the PPG signal.

In step 903, the electronic device 301 may band-pass filter a PPG signal for a certain frequency. The electronic device 301 may generate second data by band-pass filtering the first data.

In step 905, the electronic device 301 may measure biometric information (e.g., an oxygen saturation) and generate biometric information (e.g., an oxygen saturation) data.

In step 907, the electronic device 301 may analyze a waveform of a signal included in the second data, identify distortion of a signal included in the second data due to pressure applied to the sensor, and select a part corresponding to the signal for which distortion has been identified. For example, the electronic device 301 may identify signal distortion due to pressure by analyzing a waveform of a signal included in the second data and select a part (or a data part) corresponding to the identified signal.

In step 909, the electronic device 301 may provide biometric information (e.g., an oxygen saturation) while excluding a part corresponding to the signal distortion. In step 909, the electronic device 301 may display, on the display, biometric information (e.g., an oxygen saturation) data while excluding a part corresponding to the signal distortion. Further, the electronic device 301 may inform that the corresponding data has an error by blurring a part corresponding to the signal distortion or providing additional information.

Figure 10:
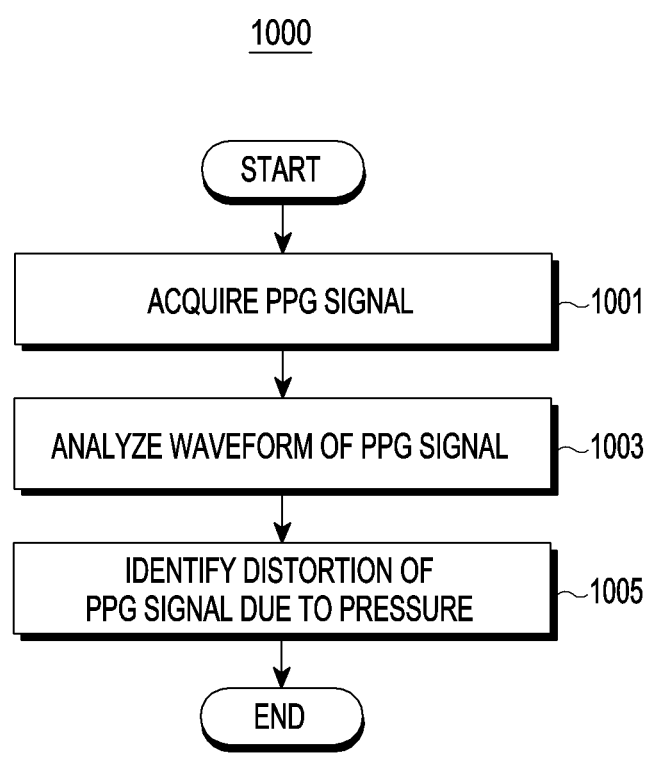
FIG. 10 is a flowchart of a method of an electronic device identifying distortion of a PPG signal according to an embodiment.

FIG. 10 is a flowchart 1000 of a method of an electronic device identifying distortion of a PPG signal according to an embodiment.

Referring to FIG. 10, in step 1001, an electronic device may acquire a PPG signal through a sensor 310. For example, the electronic device 301 may acquire PPG signals for an infrared ray signal and a red light signal. For example, the electronic device 301 may acquire first data corresponding to the PPG signal.

In step 1003, the electronic device 301 may analyze a waveform of a signal included in the first data. For example, the electronic device 301 may analyze a signal waveform included in the first data, on which separate filtering is not performed, to identify signal distortion due to pressure applied to the sensor 310. For example, the electronic device 301 may select a certain period of time (e.g., a section for one period of time or a section for integer times of one period of time) from the signal included in the first data, and analyze the shape of the waveform of a signal included in the selected period of time.

In step 1005, the electronic device 301 may analyze a waveform of a signal included in the first data, and identify distortion of a PPG signal due to pressure. A method for, by the electronic device 301, identifying distortion of a PPG signal due to pressure by analyzing a waveform of a signal included in first data is described below in greater detail with reference to FIGS. 11A to 11E.

Figure 11A:
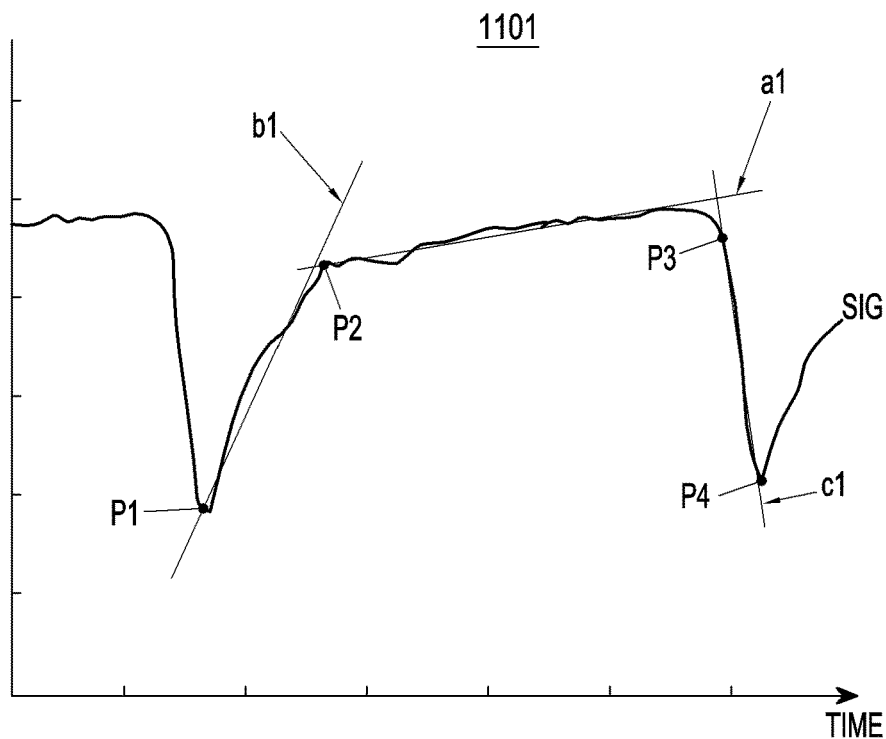
FIG. 11A is a graph of an electronic device identifying distortion of a PPG signal according to an embodiment.
Figure 11B:
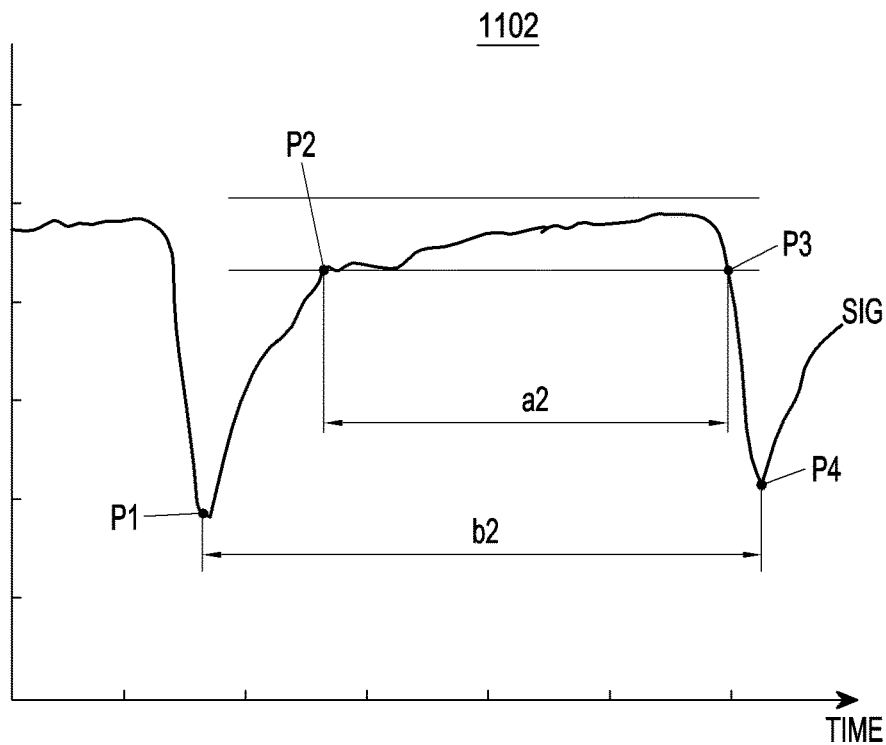
FIG. 11B is a graph of an electronic device identifying distortion of a PPG signal according to an embodiment.
Figure 11C:
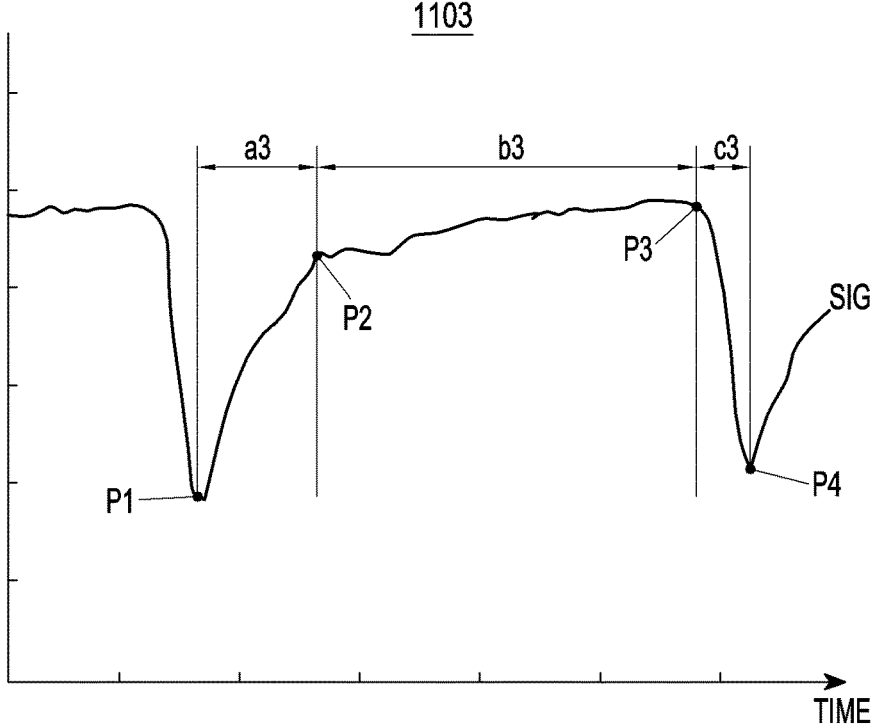
FIG. 11C is a graph of an electronic device identifying distortion of a PPG signal according to an embodiment.
Figure 11D:
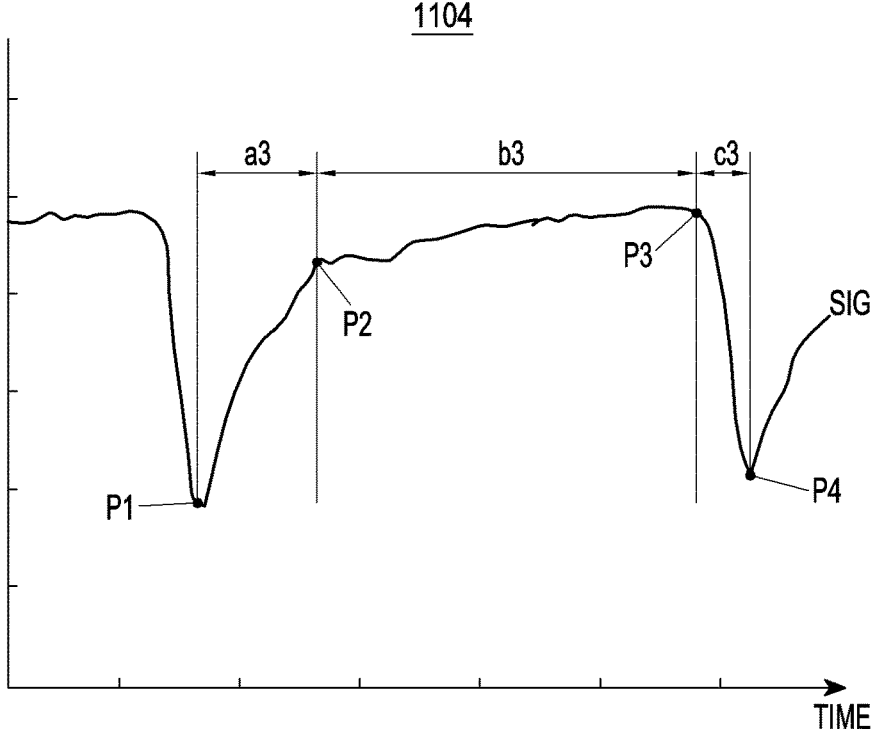
FIG. 11D is a graph of an electronic device identifying distortion of a PPG signal according to an embodiment.
Figure 11E:
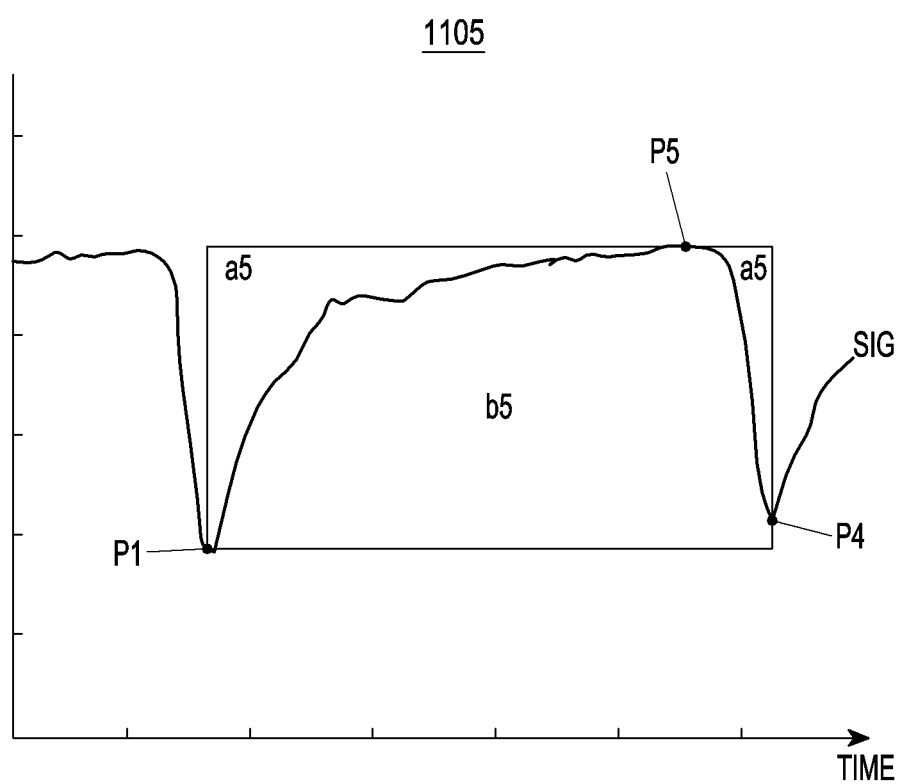
FIG. 11E is a graph of an electronic device identifying distortion of a PPG signal according to an embodiment.

FIG. 11A is a graph 1101 of a method of an electronic device identifying distortion of a PPG signal according to an embodiment, FIG. 11B is a graph 1102 of a method of an electronic device identifying distortion of a PPG signal according to an embodiment, FIG. 11C is a graph 1103 of a method of an electronic device identifying distortion of a PPG signal according to an embodiment, FIG. 11D is a graph 1104 of a method of an electronic device identifying distortion of a PPG signal according to an embodiment, and FIG. 11E is a graph 1105 of a method of an electronic device identifying distortion of a PPG signal according to an embodiment.

Referring to FIGS. 11A to 11E, an electronic device 301 may set three sections based on a first point P1, a second point P2, a third point P3, and a fourth point P4 in a time section corresponding to one period of the PPG signal SIG. For example, the first point P1, the second point P2, the third point P3, and the fourth point P4 may be branch points at which rapid changes (e.g., inclinations of the points) of the PPG signal SIG are generated. The first point P1, the second point P2, the third point P3, and the fourth point P4 may be determined by analyzing the PPG signal SIG included in a time section corresponding to one period.

Referring to FIG. 11A, the electronic device 301 may acquire lines for the sections by using a least squares method using the points included in the sections. For example, the electronic device 301 may acquire a first line having an inclination (b1) in a first section between the first point P1 and the second point P2, a second line having an inclination (a1) in a second section between the second point P2 and the third point P3, and a third line having an inclination (c1) in a third section between the third point P3 and the fourth point P4. The electronic device 301 may, if a1/b1 is less than a certain first value and a1/|c1| is less than a certain second value, determine that signal distortion is generated by pressure applied to the sensor 310.

Referring to FIG. 11B, the electronic device 301 may determine a section between the second point P2 and the third point P3 as a2, and determine a section between the first point P1 and the fourth point P4 as b2. For example, a2 may refer to a time section having a certain superior value from the maximum value of the PPG signal SIG, and b2 may refer to a section for one period of the PPG signal SIG. The electronic device 301 may, if a2/b2 is greater than a certain value, determine that signal distortion is generated by pressure applied to the sensor 310.

Referring to FIG. 11C, The electronic device 301 may determine a time section between the first point P1 and the second point P2 as section a3, determine a time section between the second point P2 and the third point P3 as section b3, and determine a time section between the third point P3 and the fourth point P4 as section c3. For example, the electronic device 301 may, if a3/b3 is less than a certain third value and c3/b3 is less than a certain fourth value, determine that signal distortion is generated by pressure applied to the sensor 310.

Referring to FIG. 11D, the electronic device 301 may determine a time section between the first point P1 and the second point P2 as section a3, determine a time section between the second point P2 and the third point P3 as section b3, and determine a time section between the third point P3 and the fourth point P4 as section c3. For example, the electronic device 301 may determine an average value of the absolute values of the differences of the two points that are adjacent to each other in section a3 as Da, determine an average value of the absolute values of the differences of the two points that are adjacent to each other in section b3 as Db, and determine an average value of the absolute values of the differences of the two points that are adjacent to each other in section c3 as Dc. For example, the electronic device 301 may, if Db/Da is less than a certain fifth value and Db/Dc is less than a certain sixth value, determine that signal distortion is generated by pressure applied to the sensor 310.

Referring to FIG. 11E, the electronic device 301 may determine a rectangular region based on a maximum value P5 and two minimum values P1 and P4 of the PPG signal SIG of one period. The electronic device 301 may determine the area of the outer region of the PPG signal SIG as a5, and determine the area of the inner region of the PPG signal SIG as b5 in the determination region. For example, the electronic device 301 may, if a5/b5 is less than a certain value, determine that signal distortion is generated by pressure applied to the sensor 310.

Although FIGS. 11A to 11E illustrate that the points that divide the sections or regions of the PPG signal as the first point P1, the second point P2, the third point P3, and the fourth point P4, the illustration is simply for convenience of description, and the locations or the number of the corresponding points may not be limited according to a measurement method.

Figure 12A:
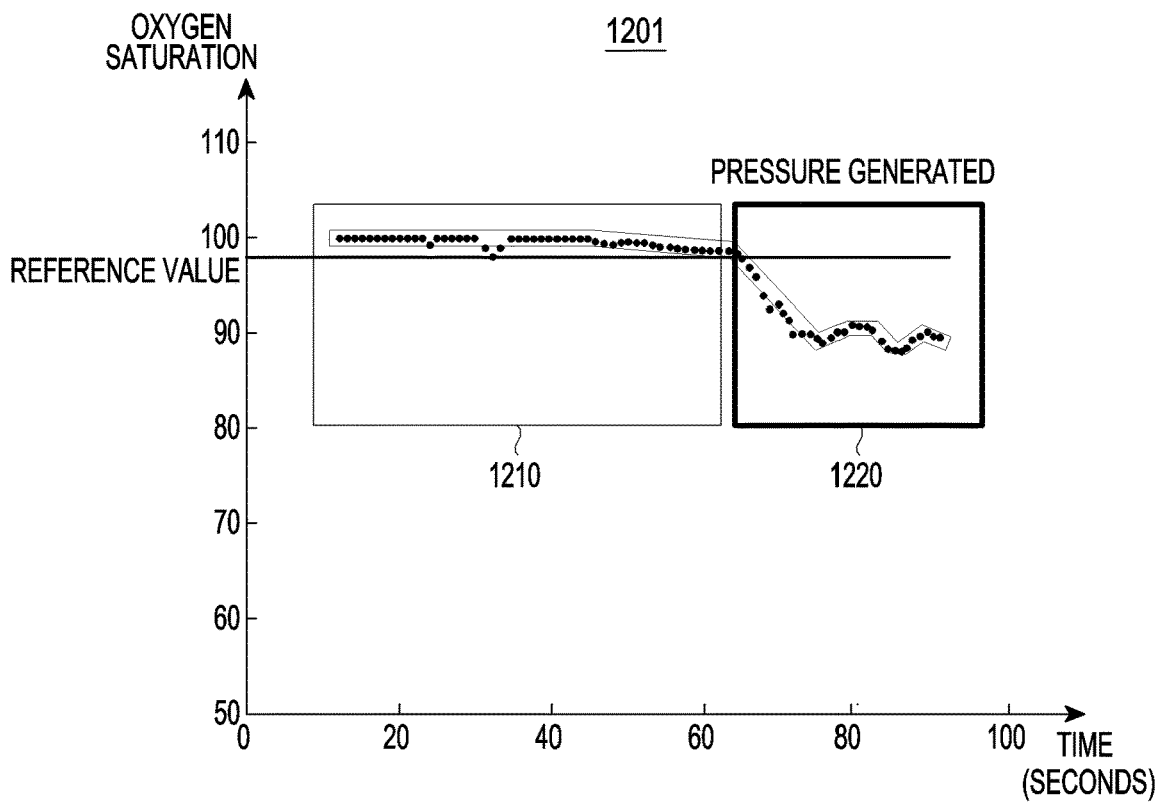
FIG. 12A is a graph of an electronic device providing biometric information according to an embodiment.
Figure 12B:
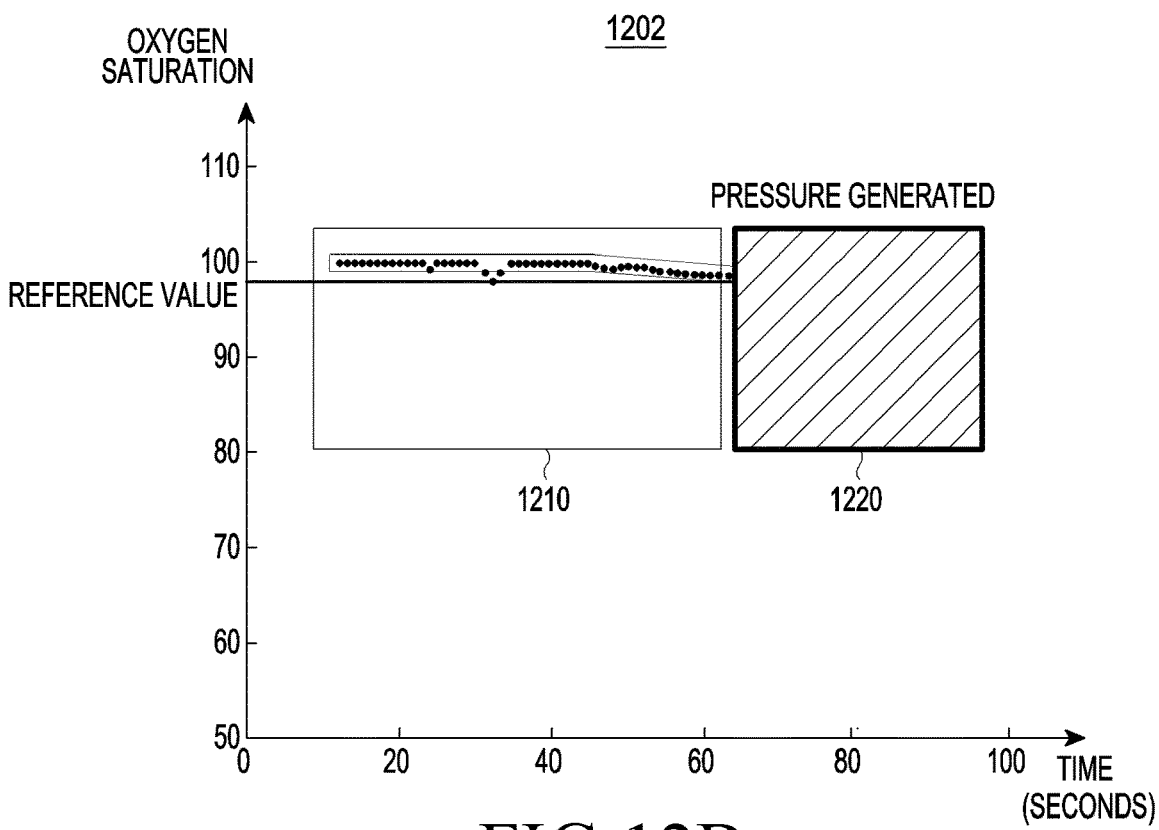
FIG. 12B is a graph of an electronic device providing biometric information according to an embodiment.

FIG. 12A is a graph 1201 of a method of an electronic device providing biometric information according to an embodiment, and FIG. 12B is a graph 1202 of a method of an electronic device providing biometric information according to an embodiment.

Referring to FIGS. 12A and 12B, an electronic device 301 may generate data for biometric information (e.g., an oxygen saturation) based on the PPG signal acquired through a sensor 310.

The electronic device 301 may measure biometric information (e.g., an oxygen saturation) while not identifying signal distortion due to pressure applied to the sensor 310.

Referring to FIG. 12A, in the first section 1210 in which pressure is not generated, the measured oxygen saturation values may be values that are approximate to a reference value. In the second section 1220 in which pressure is generated, the measured oxygen saturation values may be values that are different from the reference value. That is, it may be identified that the oxygen saturation values measured in the second section 1220 in which pressure is generated have errors with reference to the reference value. For example, the reference value may be a value corresponding to a normal range of oxygen saturation in everyday lives and may be an oxygen saturation value of another body portion in a normal pressure range.

Referring to FIG. 12B, the electronic device 301 may not provide data of a part in which signal distortion is generated by pressure. For example, the electronic device 301 may select a part, for which signal distortion has been identified, by identifying signal distortion by pressure after generating oxygen saturation data. The electronic device 301 may provide oxygen saturation data of the first section 1210, in which no pressure is generated, and may not provide data of the second section 1220, in which pressure is generated. Further, the electronic device 301 may distinguish (e.g., through blurring) the data of the second section 1220, in which pressure is generated, from the data of the first section, and provide the data of the second section 1220.

Figure 13:
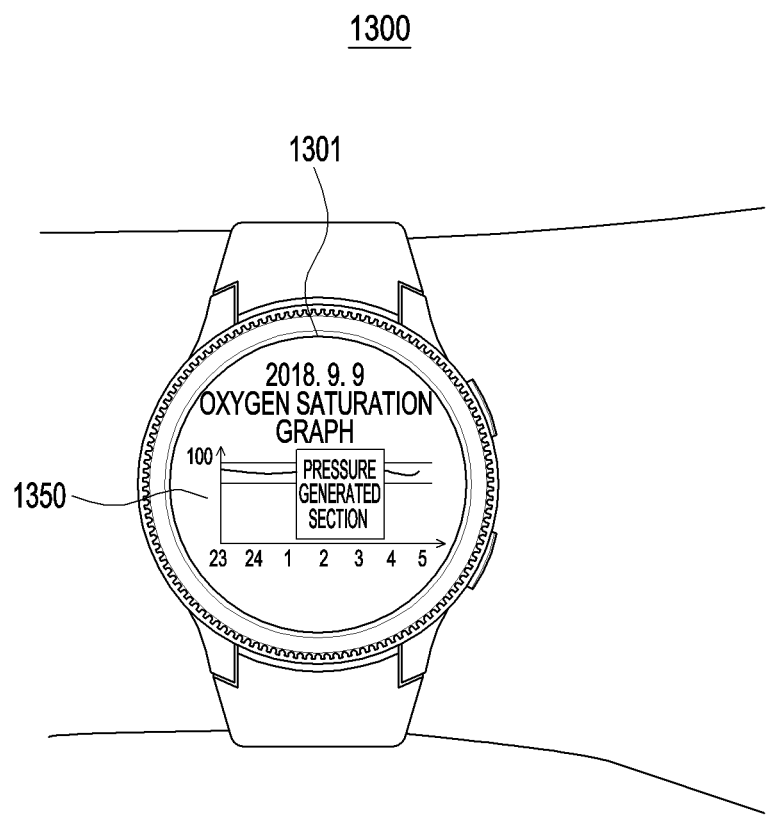
FIG. 13 is an illustration of a user interface of an electronic device providing biometric information according to an embodiment.

FIG. 13 is an illustration 1300 of a user interface of an electronic device for providing biometric information according to an embodiment.

Referring to FIG. 13, the electronic device 1301 may display biometric information (e.g., an oxygen saturation) data through a graphical user interface 1350. For example, the electronic device 1301 may be implemented in a manner that is the same as or similar to the electronic device 101 of FIG. 1 and/or the electronic device 301 of FIG. 3.

The electronic device 1301 may not provide data of a portion at which signal distortion by pressure is generated. For example, the electronic device 1301 may, after generating oxygen saturation data, identify, in advance, a part in which signal distortion is generated due to pressure applied to a body by the sensor (or a sensor contact surface). Further, the electronic device 1301 may provide, through the graphical user interface 1350, only oxygen saturation data of the section in which no pressure is generated and may not provide data of the section in which pressure is generated. The electronic device 1301 may provide, through the graphical user interface 1350, information (e.g., blurring, shading, boxing, and/or notification) on the section in which pressure is generated. Further, the electronic device 1301 may process the section, in which pressure is generated, such that the section is distinguished by a color or a form (e.g., a dotted line) that is different from that of the previous graphs, in the graphical user interface 1350.

Figure 14A:
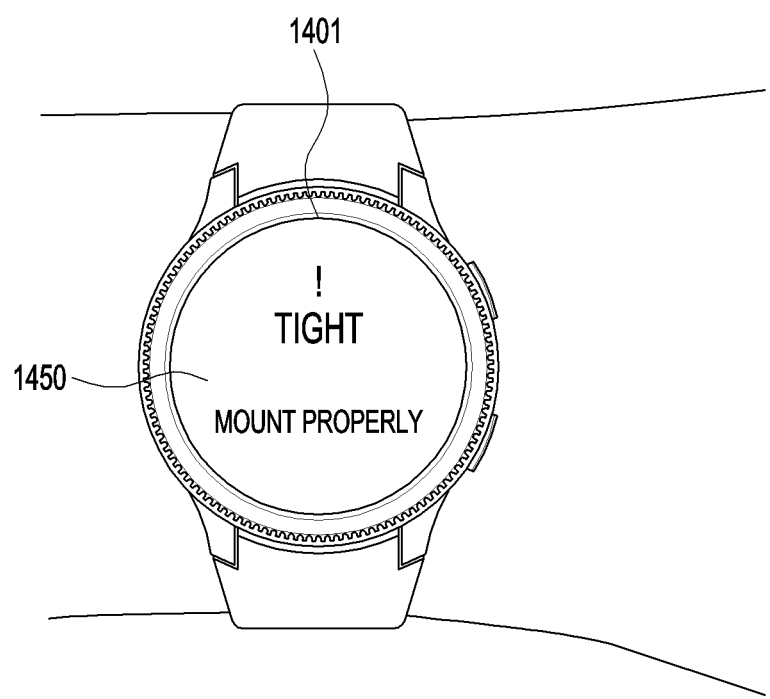
FIG. 14A is an illustration of a user interface of an electronic device providing a guide for measuring biometric information according to an embodiment.
Figure 14B:
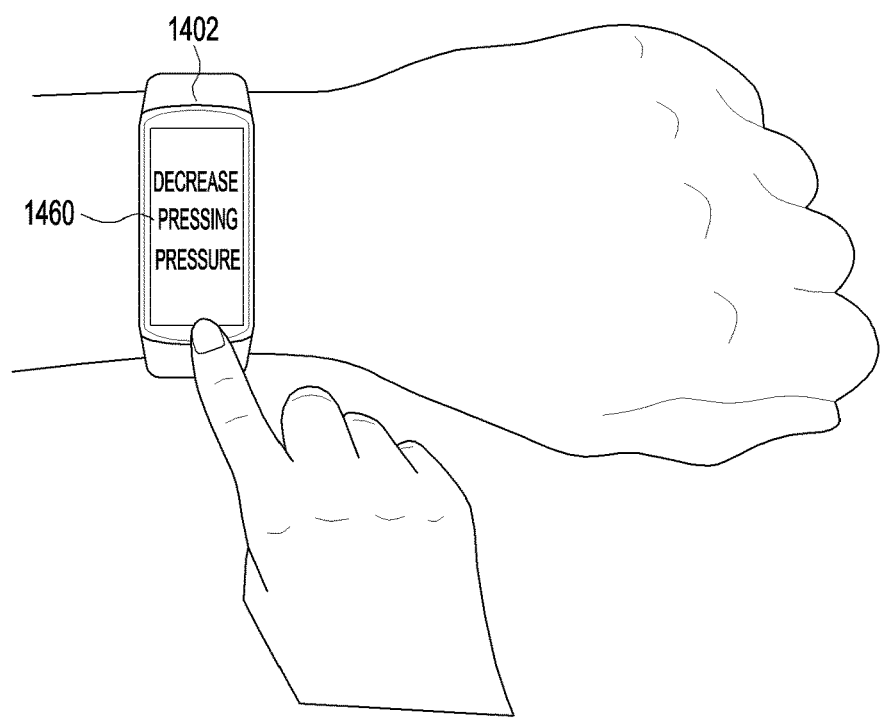
FIG. 14B is an illustration of a user interface of an electronic device providing a guide for measuring biometric information according to an embodiment.

FIG. 14A is an illustration 1400-1 of a user interface of an electronic device providing a guide for measuring biometric information according to an embodiment, and FIG. 14B is an illustration 1400-2 of a user interface of an electronic device providing a guide for measuring biometric information according to an embodiment.

Referring to FIG. 14A, the electronic device 1401 may provide a guide for measuring biometric information through a user interface 1450.

The electronic device 1401 may identify or determine pressure generated according to a degree, where a sensor 1411 provided on a rear surface of the electronic device 1401 and a wrist part of the user are in contact with each other when biometric information is measured.

If pressure generated in the sensor 1411 provided on the rear surface of the electronic device 1401 and the wrist part of the user is greater than a certain value, the electronic device 1401 may provide a guide. For example, the electronic device 1401 may, through the guide, suggest that the mounting state of the electronic device 1401 be loosened or adjusted properly because the wearing state of the electronic device 1401 is too tight. Further, the electronic device 1401 may, through the guide, suggest that the mounting state of the electronic device 1401 be tightened or adjusted properly because the wearing state of the electronic device is too loose.

Referring to FIG. 14B, the electronic device 1402 may provide a guide for measuring biometric information through a user interface 1460.

The electronic device 1402 may identify or determine pressure generated according to a degree, where a sensor 1412 provided on a front surface of the electronic device 1402 and a finger of the user contact each other when biometric information is measured.

If the pressure generated in the sensor 1412 provided on the front surface of the electronic device 1402 and the finger of the user is greater than a certain value, the electronic device 1402 may provide a guide. For example, the electronic device 1402 may suggest, through the guide, that a force (or pressure) with which the finger is pressed be decreased. Further, when the pressure with which the finger is pressed is too weak, the electronic device 1402 may suggest, through the guide, that the force (or pressure) with which the finger is pressed be increased.

The electronic device 1401 or 1402 may determine a threshold value for identifying signal distortion by pressure differently according to a situation in which biometric information is measured. For example, the electronic device 1401 or 1402 may determine that the threshold value to be high in a state (e.g., a movement state) in which the user moves a lot and may determine the threshold value to be low in a state (e.g., a sleeping state) in which the user moves little.

Figure 15:
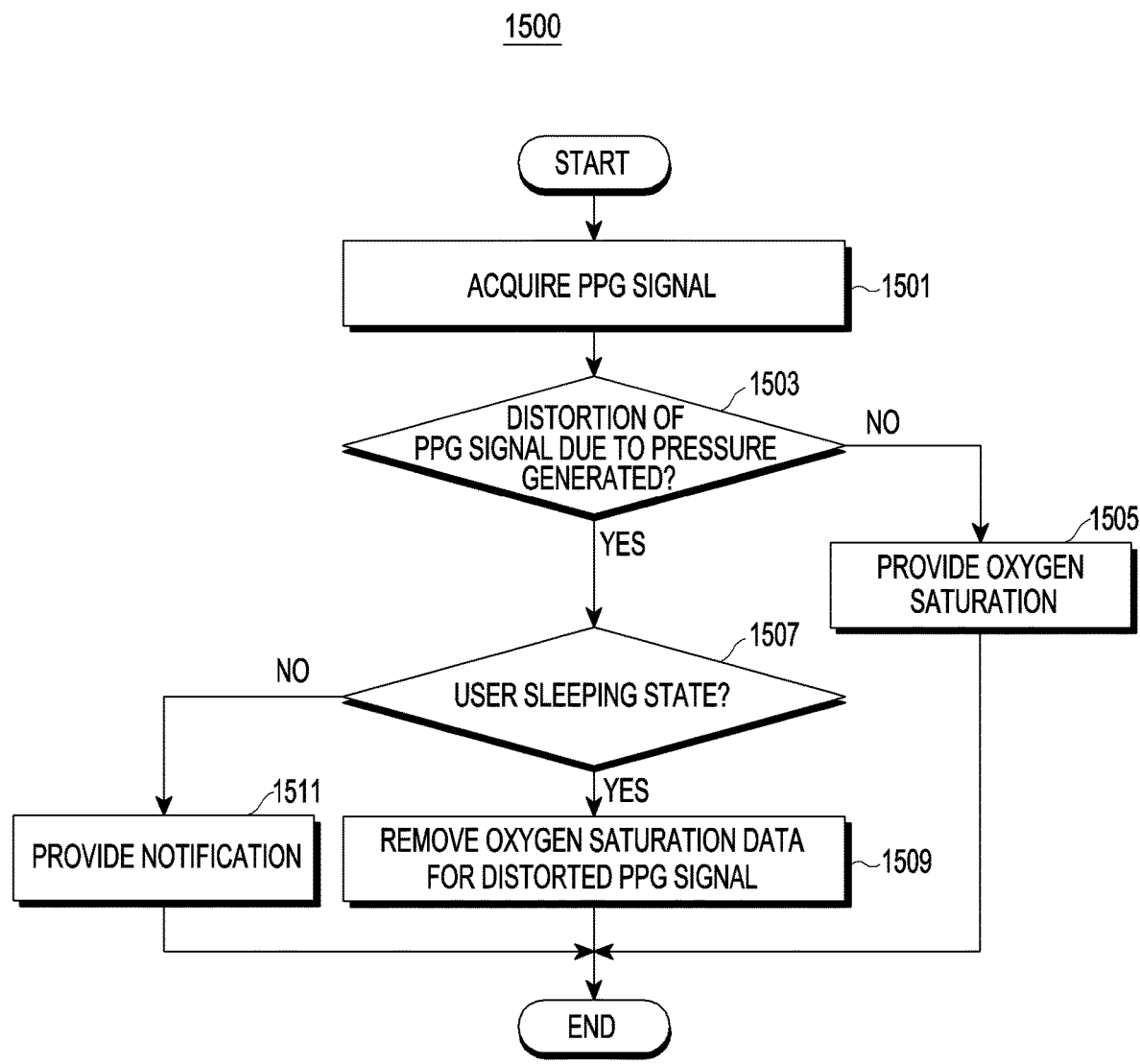
FIG. 15 is a flowchart of a method of an electronic device providing biometric information according to distortion of a PPG signal according to an embodiment.

FIG. 15 is a flowchart 1500 of a method of an electronic device providing biometric information according to distortion of a PPG signal according to an embodiment.

Referring to FIG. 15, in step 1501, an electronic device may acquire a PPG signal through a sensor.

In step 1503, the electronic device 301 may identify distortion of the PPG signal due to pressure applied to a body by the sensor 310. For example, the electronic device 301 may band-pass filter a signal acquired in a certain period of time of the PPG signal and may identify distortion of the band-pass filtered light signal due to pressure by comparing a ratio of a positive maximum amplitude and a negative maximum amplitude of the signal with a threshold value. Further, the electronic device 301 may identify distortion of the PPG signal by using the method described above with reference to FIGS. 11A to 11E.

In step 1505, if there is no distortion of the PPG signal due to pressure (e.g., NO in step 1503), the electronic device 301 measures or identifies biometric information (e.g., an oxygen saturation). Further, the electronic device 301 may provide and/or store the measured or identified biometric information (e.g., an oxygen saturation) data. The electronic device 301 may, when the measured oxygen saturation is less than a reference value, provide a notification that indicates degradation of an oxygen saturation. For example, the electronic device 301 may provide a notification through at least one of a popup window, a vibration, and a sound.

In step 1507, if there is distortion of the PPG signal due to pressure (e.g., YES in step 1503), the electronic device 301 may identify whether the user is in a sleeping state. For example, the electronic device 301 may identify whether the electronic device 301 is being operated in a sleeping mode that indicates the sleeping state of the user. Further, the electronic device 301 may identify whether the user is sleeping by using an acceleration sensor or a timer.

In step 1509, if it is identified that the user is in a sleeping state (e.g., YES in step 1507), the electronic device 301 may remove a PPG signal of a section in which signal distortion is generated or biometric information (e.g., an oxygen saturation) data for the PPG signal. That is, the electronic device 301 may determine that a normal measurement is not performed due to pressure generated when the measured portion is pressed by movement during sleeping in the corresponding section and may remove the PPG signal of the corresponding section and/or the biometric information (e.g., an oxygen saturation) data.

In step 1511, if it is not identified that the user is in a sleeping state (e.g., NO in step 1507), the electronic device 301 may provide a notification that informs that distortion of the PPG signal is generated due to pressure or informs that biometric information cannot be measured normally. For example, the electronic device 301 may provide a notification through at least one of a popup window, a vibration, and a sound.

Figure 16:
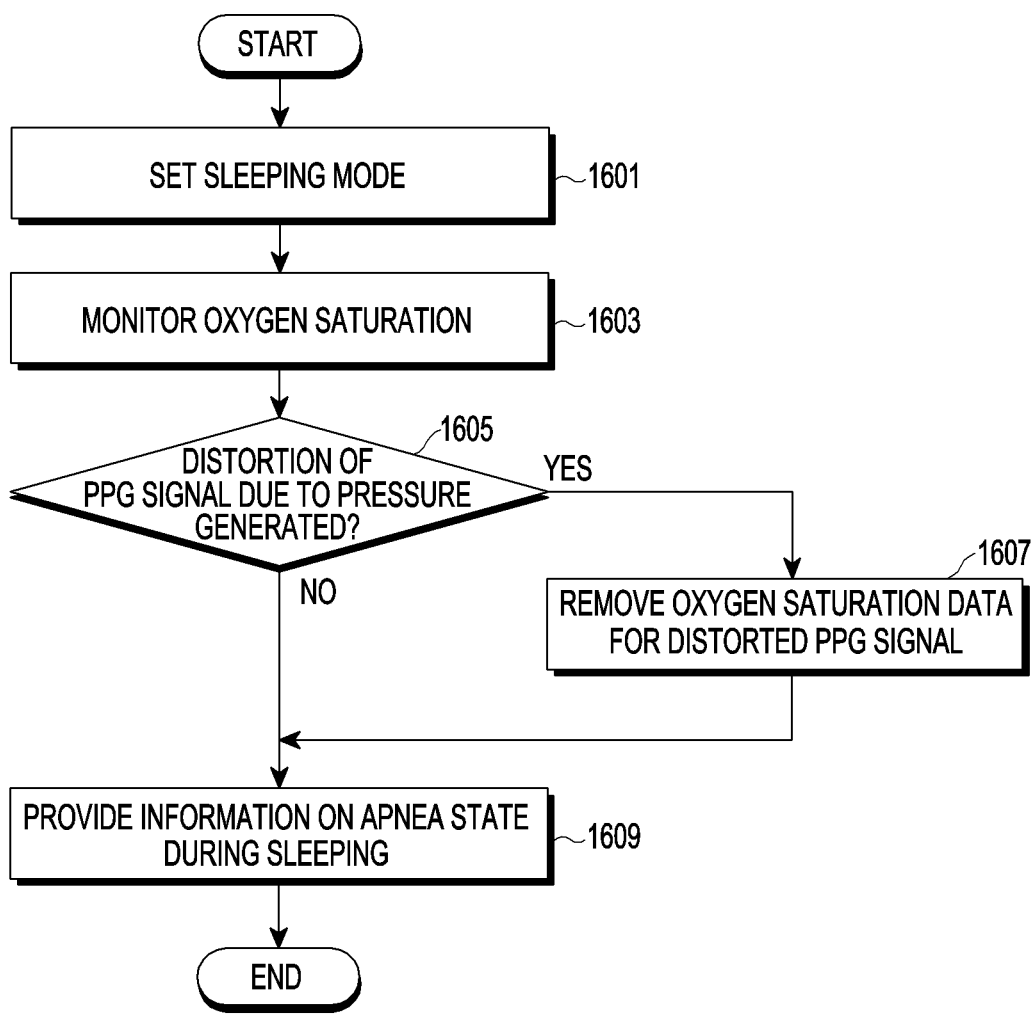
FIG. 16 is a flowchart of a method of an electronic device providing information on an apnea state according to distortion of a PPG signal according to an embodiment.

FIG. 16 is a flowchart 1600 of a method of an electronic device providing information on an apnea state according to distortion of a PPG signal according to an embodiment.

Referring to FIG. 16, step 1601, an electronic device 301 may be set to a sleeping mode. For example, the sleeping mode may refer to a mode that indicates that the user is in a sleeping mode.

In step 1603, the electronic device 301 may monitor an oxygen saturation of the user by using a sensor 310 in the sleeping mode. For example, the electronic device 301 may monitor the oxygen saturation at a preset period or in real time.

In step 1605, the electronic device 301 may identify distortion of a PPG signal due to pressure applied to a body by the sensor 310.

In step 1607, if signal distortion by pressure is identified (e.g., YES in step 1605), the electronic device 301 may remove oxygen saturation data information on the distorted PPG signal. That is, the electronic device 301 may determine that a normal measurement is not performed due to pressure caused by movement during sleeping in the corresponding section and may remove the oxygen saturation data of the corresponding section.

In step 1609, if signal distortion by pressure is not identified (e.g., NO in step 1605), the electronic device 301 may provide information on an apnea state during sleeping. For example, the electronic device 301 may provide and store information on a number and/or a duration of apnea states during sleeping.

Figure 17:
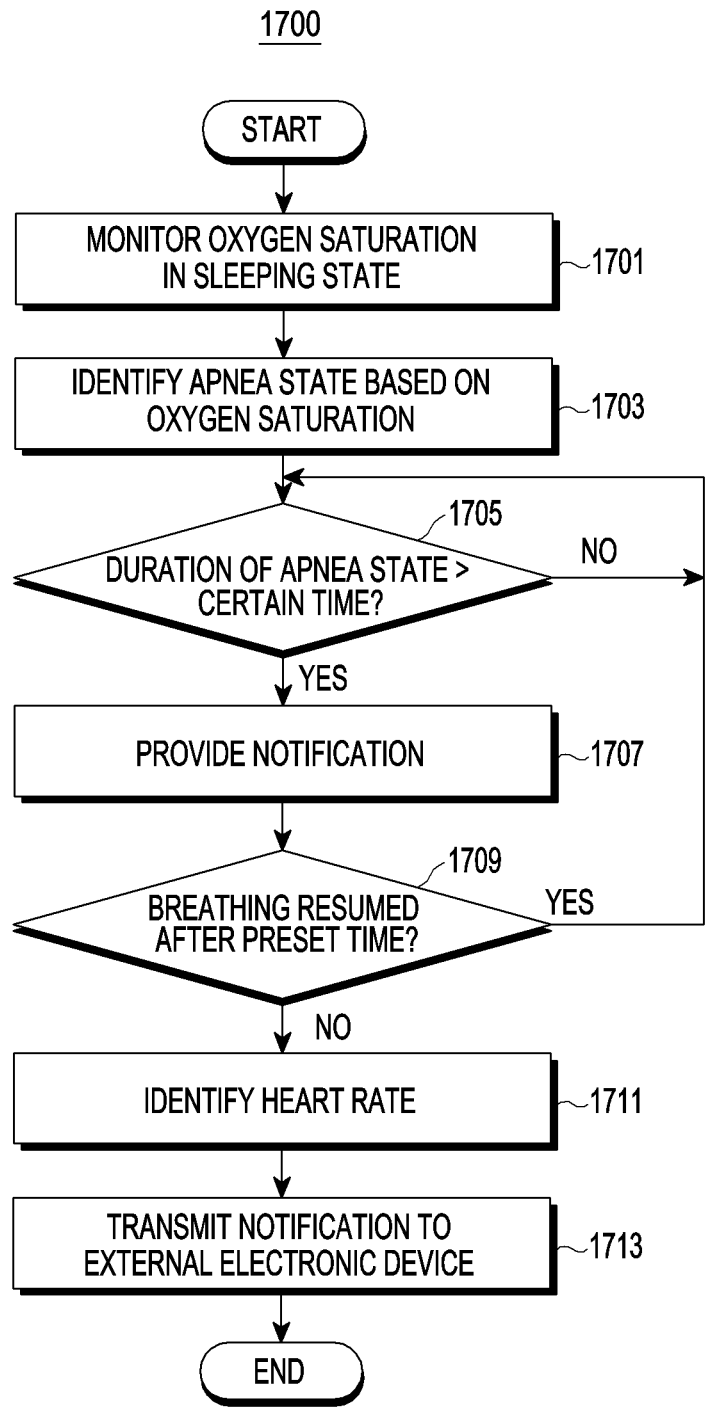
FIG. 17 is a flowchart of a method of an electronic device providing information on an apnea state according to distortion of a PPG signal according to an embodiment.

FIG. 17 is a flowchart 1700 of a method of an electronic device providing information on an apnea state according to distortion of a PPG signal according to an embodiment.

Referring to FIG. 17, in step 1701, an electronic device 301 may monitor an oxygen saturation of a user by using a sensor 310 in a sleeping state of the user.

In step 1703, the electronic device 301 may identify, based on an oxygen saturation, whether an apnea state of the user occurs. For example, the electronic device 301 may determine that an apnea state occurs when the measured oxygen saturation is less than a preset value.

In step 1705, the electronic device 301 may identify whether a duration of the apnea state is greater than a certain time. For example, the certain time may refer to a time for which the apnea state may detrimentally influence the health of the user, and the certain time may be determined automatically or manually. If the duration of the apnea state is not greater than the certain time (e.g., NO in step 1705), the electronic device 301 may subsequently identify, based on the oxygen saturation, whether an apnea state of the user occurs. Then, the electronic device 301 may provide or store information on a number and a duration of the apnea states.

In step 1707, if the duration of the apnea state is greater than the certain time (e.g., YES in step 1705), the electronic device 301 may provide a notification that indicates the apnea state in various routes. For example, the electronic device 301 may provide a notification through at least one of a popup window, a vibration, and a sound.

In step 1709, the electronic device 301 may identify, based on an oxygen saturation measured through the sensor 310, whether breathing of the user is resumed after a preset period of time. If breathing of the user is resumed within or after the preset time (e.g., YES in step 1709), the electronic device 301 may subsequently identify, based on the oxygen saturation, whether the apnea state of the user occurs.

In step 1711, if breathing of the user is not resumed after the preset time (e.g., NO of in step 1709), the electronic device 301 may identify a heart rate of the user by using the PPG signal acquired through the sensor 310.

In step 1713, the electronic device 301 may contact an emergency medical institute or transmit a message or a notification to a registered emergency contact address if the identified heart rate is greater than a certain heart rate or a statistical heart rate in a normal range in which apnea does not occur during sleeping, or the heart rate is 0 (that is, a cardiac arrest state). Further, the electronic device 301 may first provide an alarm using a sound or a vibration to wake up the user if the identified heart rate is greater than a certain heart rate or a statistical heart rate in a normal range in which apnea does not occur during sleeping, or the heart rate is 0 (that is, a cardiac arrest state). The electronic device 301 may automatically contact an emergency medical institute or transmit a message or a notification to a registered emergency contact address when there is no reaction (e.g., a reaction of turning off an alarm) of the user for a predetermined period of time even after an alarm using a sound or a vibration is provided.

Figure 18A:
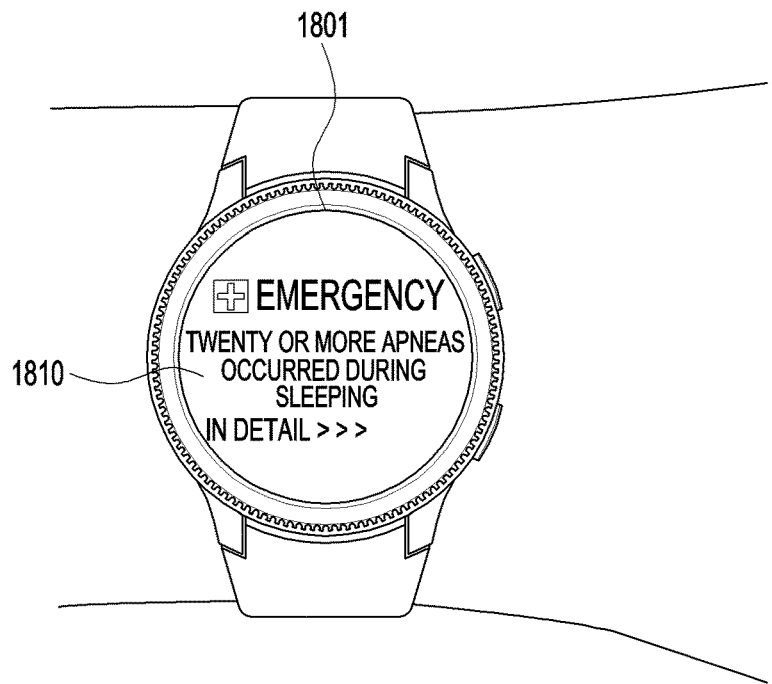
FIG. 18A is an illustration of a user interface of an electronic device providing information on an apnea state according to an embodiment.
Figure 18B:
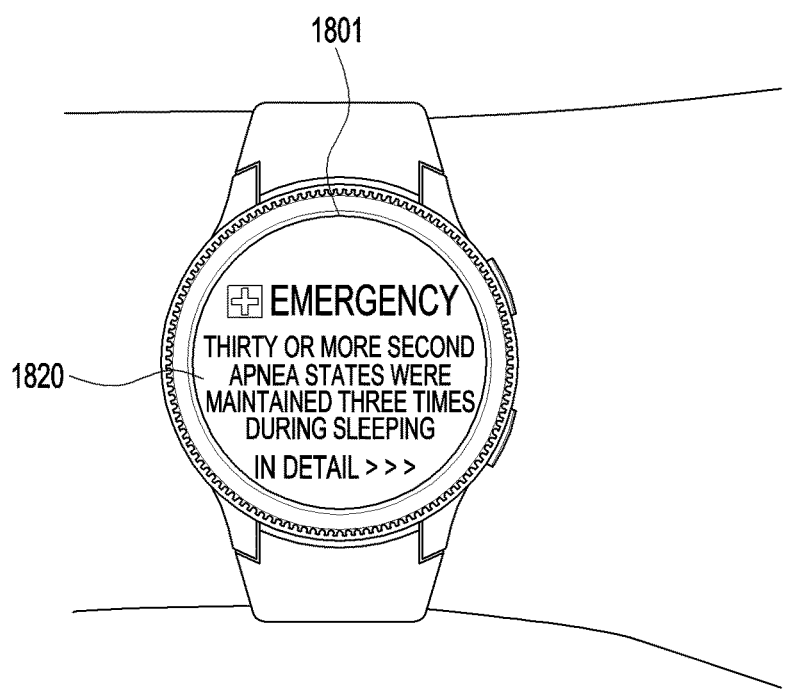
FIG. 18B is an illustration of a user interface of an electronic device providing information on an apnea state according to an embodiment.
Figure 18C:
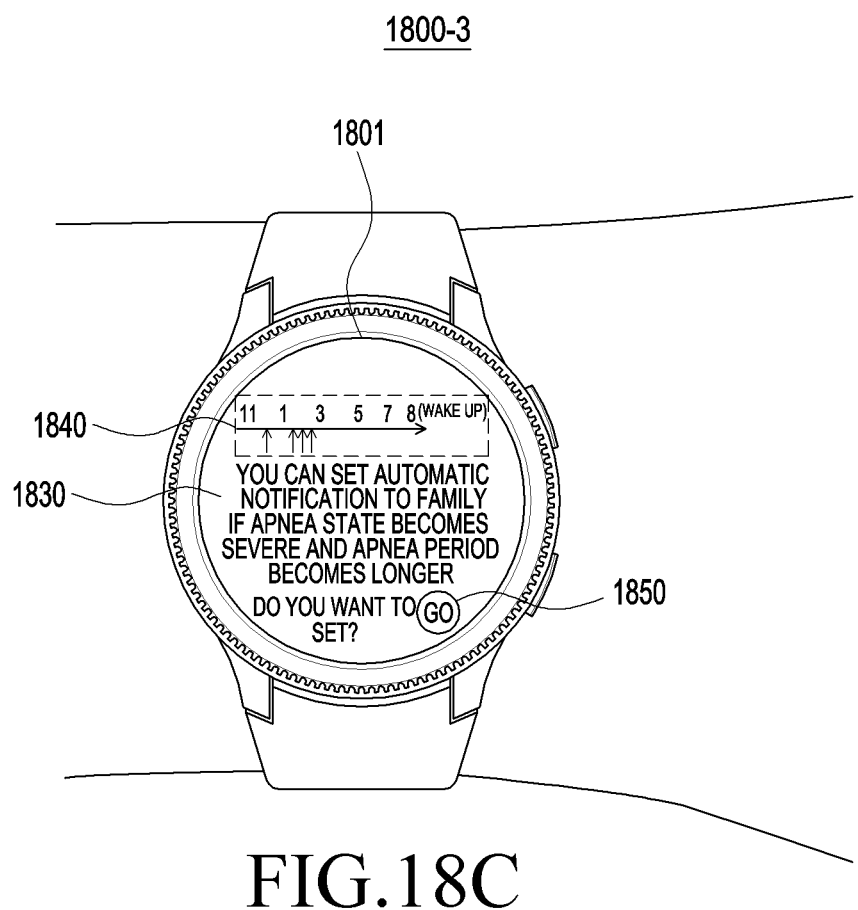
FIG. 18C is an illustration of a user interface of an electronic device providing information on an apnea state according to an embodiment.

FIG. 18A is an illustration 1800-1 of a user interface of an electronic device providing information on an apnea state according to an embodiment, FIG. 18B is an illustration 1800-2 of a user interface of an electronic device providing information on an apnea state according to an embodiment, and FIG. 18C is an illustration 1800-3 of a user interface of an electronic device providing information on an apnea state according to an embodiment.

Referring to FIG. 18A, the electronic device 1801 may display, on a display 360, a user interface 1810 including information on a number of apnea states during sleeping.

Referring to FIG. 18B, the electronic device 1801 may display, on a display 360, a user interface 1802 including information on a duration and a number of apnea states during sleeping.

The electronic device 1801 may determine whether the duration and the number of apnea states correspond to a dangerous state during sleeping. The electronic device 1801 may, when it is determined that the state of the user is dangerous, output an alarm through a peripheral Internet of things (IoT) device. For example, when it is determined that the user is in a dangerous state, the electronic device 1801 may transmit a command for controlling the IoT device such that a warning alarm is generated through the peripheral IoT device (e.g., an artificial intelligence (AI) speaker).

Referring to FIG. 18C, the electronic device 1801 may provide a user interface 1830 for setting an emergency contact address in an emergency situation due to an apnea state during sleeping. Then, the electronic device 1801 may provide an interface for setting an emergency contact address in response to an input (e.g., a touch) for an object 1850. Further, the electronic device 1801 may provide information 1840 including information that indicates a time at which an apnea state occurs during sleeping.

The user may directly set at least one of a threshold value of an oxygen saturation, a threshold value for a duration of an apnea state, and a threshold value for a number of apnea states according to a degree of the apnea state of the electronic device 1801. Further, the corresponding threshold values may be automatically determined according to an input (e.g., recognition or ignorance of an alarm of an apnea state) of the user.

According to an embodiment, an electronic device includes a housing, a touchscreen display viewable through a first part of the housing, a PPG sensor exposed through a second part of the housing, a processor disposed in the housing and operatively connected to the touchscreen display and the PPG sensor, and a memory disposed in the housing and operatively connected to the processor, where the memory stores instructions that, when executed, are configured to cause the processor to receive first data from the PPG sensor, generate second data by band-pass filtering the first data, generate oxygen saturation data based on at least some of the second data, select a first portion related to a first period of time from the second data, and display, on the touchscreen display, a graphical user interface including information related to the oxygen saturation data except for data corresponding to the first portion from the graphical user interface.

The instructions may be configured to cause the processor to select the first portion based on at least a portion of a waveform of a signal included in the second data.

The instructions may be configured to cause the processor to select the first portion based on the at least a portion of the width of the signal.

The instructions may be configured to cause the processor to select the first portion by comparing a ratio of a positive maximum amplitude and a negative maximum amplitude of the signal in the first period time with a threshold value.

The instructions may be configured to cause the processor to recognize that the first portion is a portion distorted by pressure and store the oxygen saturation data based on the recognized first portion.

The instructions may be configured to cause the processor to identify signal distortion due to pressure applied to a body of a user by the PPG sensor based on the at least a portion of the amplitude of a signal corresponding to the first portion included in the second data.

The instructions may be configured to cause the processor to identify the signal distortion by comparing ratios of positive maximum amplitudes and negative maximum amplitudes of signals corresponding to an infrared ray and a red color included in the first portion of the oxygen saturation data with corresponding threshold values.

The instructions may be configured to cause the processor to, in response to identifying the signal distortion, provide a guide that informs that pressure causing signal distortion is generated between the PPG sensor and the body of the user.

The instructions may be configured to cause the processor to, in response to identifying that the user is in a sleeping state, determine an apnea state during sleeping based on the oxygen saturation data except for the data corresponding to the first portion.

The instructions may be configured to cause the processor to, when the duration of the apnea state is greater than a preset time, provide a notification on the apnea state.

According to an embodiment, a method for operating an electronic device includes receiving first data from a PPG sensor of the electronic device, generating second data by band-pass filtering the first data, generating oxygen saturation data based on the at least some of the second data, selecting a first portion related to a first period of time from the second data, and displaying, on the touchscreen display, a graphical user interface including information related to the oxygen saturation data except for data corresponding to the first portion from the graphical user interface.

Selecting the first portion may include selecting the first portion based on the at least a portion of the amplitude of a signal included in the second data.

Selecting the first portion may include selecting the first portion by comparing a ratio of a positive maximum amplitude and a negative maximum amplitude of the signal included in the second data in the first period time with a threshold value.

The method for operating the electronic device may further include identifying signal distortion due to pressure applied to a body of a user by the PPG sensor based on the at least a portion of the amplitude of a signal corresponding to the first portion of the second data.

The method for operating the electronic device may further include providing a guide that informs that pressure that generates signal distortion is generated between the PPG sensor and the body of the user.

According to an embodiment, an electronic device includes a PPG sensor, a processor, and a memory operatively connected to the processor, where the memory stores instructions that, when executed, are configured to cause the processor to acquire a PPG signal for a user from the PPG sensor, identify signal distortion of first data due to pressure applied to a body of a user by the PPG sensor, based on the at least a portion of second data generated by band-pass filtering the first data corresponding to the PPG signal, and in response to identifying that there is no signal distortion of the first data, identify biometric information by using the PPG signal.

The instructions may be configured to cause the processor to, in response to identifying that there is signal distortion of the first data, refrain from identifying biometric information by using the PPG signal.

The instructions may be configured to cause the processor to, in response to identifying that there is signal distortion of the first data, provide the biometric information except for the first data corresponding to the first period of time.

The instructions may be configured to cause the processor to identify signal distortion of the first data based on a waveform of a signal included in the second data.

The instructions may be configured to cause the processor to identify signal distortion of the first data due to pressure on the PPG sensor by a ratio of a positive maximum amplitude and a negative maximum amplitude of the signal with a preset threshold in the first period of time.

The instructions may be configured to cause the processor to, in response to identifying that the biometric information identified by using the PPG signal satisfies a certain condition related to a danger to the health of the user when there is no signal distortion of the first data, provide an alarm.

Each of the components of the electronic device according to the present disclosure may be implemented by one or more components and a name of the corresponding component may vary depending on a type of the electronic device. In various embodiments, the inspection apparatus may include at least one of the above-described elements. Some of the above-described elements may be omitted from the electronic device, or the inspection apparatus may further include additional elements. Further, some of the components of the electronic device according to the various embodiments of the present disclosure may be combined to form a single entity and thus may equivalently execute functions of the corresponding elements prior to the combination.

The embodiments disclosed herein are provided merely to easily describe the present disclosure and to facilitate understanding of the present disclosure, but are not intended to limit the scope of the present disclosure. Therefore, it should be construed that all modifications and changes or modified and changed forms based on the present disclosure fall within the scope of the present disclosure as defined by the appended claims and their equivalents.

What is claimed is:

1. An electronic device, comprising:
a housing;
a touchscreen display viewable through a first part of the housing;
a photoplethysmogram (PPG) sensor exposed through a second part of the housing;
a processor disposed in the housing and operatively connected to the touchscreen display and the PPG sensor; and
a memory disposed in the housing and operatively connected to the processor,
wherein the memory is configured to store instructions that, when executed, are configured to cause the processor to:
receive first data from the PPG sensor;
generate second data by band-pass filtering the first data;
identify signal distortion due to pressure applied to a body of a user by the PPG sensor based on at least a portion of an amplitude of at least one signal corresponding to a first portion of the second data, wherein the first portion is determined based on comparing a ratio of a positive maximum amplitude and a negative maximum amplitude of at least one signal corresponding to the second data with a threshold value;
when there is the signal distortion, identify whether the electronic device is set to a sleeping mode indicating the user is in a sleeping state;
when the electronic device is set to the sleeping mode, generate oxygen saturation data based on at least some of the second data;
display, on the touchscreen display, a graphical user interface comprising information related to the oxygen saturation data except for data corresponding to the first portion from the graphical user interface, and
wherein the first portion is a portion distorted by the pressure.

2. The electronic device of claim 1, wherein the instructions, when executed, are further configured to cause the processor to:
determine the first portion based on at least a portion of a width of the at least one signal.

3. The electronic device of claim 1, wherein the instructions, when executed, are further configured to cause the processor to:
store the oxygen saturation data based on the identified first portion.

4. The electronic device of claim 1, wherein the instructions, when executed, are further configured to cause the processor to:
identify the signal distortion by comparing ratios of positive maximum amplitudes and negative maximum amplitudes of signals corresponding to an infrared ray and a red color included in the first portion of the oxygen saturation data with corresponding threshold values.

5. The electronic device of claim 1, wherein the instructions, when executed, are further configured to cause the processor to:
based on identifying the signal distortion, provide a guide that informs that pressure causing the signal distortion is generated between the PPG sensor and the body of the user.

6. The electronic device of claim 1, wherein the instructions, when executed, are further configured to cause the processor to:
determine an apnea state during sleeping based on the oxygen saturation data except for the data corresponding to the first portion.

7. The electronic device of claim 6, wherein the instructions, when executed, are further configured to cause the processor to:
when a duration of the apnea state is greater than a preset time, provide a notification on the apnea state.

8. A method for operating an electronic device, the method comprising:
receiving first data from a photoplethysmogram (PPG) sensor of the electronic device;
generating second data by band-pass filtering the first data;
identifying signal distortion due to pressure applied to a body of a user by the PPG sensor based on at least a portion of an amplitude of at least one signal corresponding to a first portion of the second data, wherein the first portion is determined based on comparing a ratio of a positive maximum amplitude and a negative maximum amplitude of at least one signal corresponding to the second data with a threshold value;
when there is the signal distortion, identifying whether the electronic device is set to a sleeping mode indicating the user is in a sleeping state;
when the electronic device is set to the sleeping mode, generating oxygen saturation data based on at least some of the second data; and
displaying, on a touchscreen display, a graphical user interface comprising information related to the oxygen saturation data except for data corresponding to the first portion from the graphical user interface,
wherein the first portion is a portion distorted by pressure.

9. An electronic device, comprising:
a photoplethysmogram (PPG) sensor;
an acceleration sensor;
a display;
a processor operatively connected to the PPG sensor; and
a memory operatively connected to the processor,
wherein the memory is configured to store instructions that, when executed, are configured to cause the processor to:
receive first data from the PPG sensor;
generate second data by band-pass filtering the first data;
identify whether signal distortion of the first data due to pressure applied to a body of a user by the PPG sensor, based on at least a portion of an amplitude of at least one signal corresponding to a first portion included in the second data, wherein the first portion is determined based on comparing a ratio of a positive maximum amplitude and a negative maximum amplitude of at least one signal corresponding to the second data with a threshold value; and
when there is the signal distortion, identify whether the user is sleeping using the acceleration sensor;
when the user is sleeping, generate oxygen saturation data based on at least some of the second data; and
display, on the display, a graphical user interface comprising information related to the oxygen saturation data except for data corresponding to the first portion from the graphical user interface, wherein the first portion is a portion distorted by pressure.

10. The electronic device of claim 9, wherein the instructions, when executed, are further configured to cause the processor to:

based on identifying that the user is not sleeping, refrain from generating oxygen saturation data using the second data.

11. The electronic device of claim 9, wherein the instructions, when executed, are further configured to cause the processor to:

based on identifying that the oxygen saturation data satisfies a condition related to a danger to health of the user when there is no signal distortion of the first data or the second data, provide an alarm to an external device.

* * * * *